(12) United States Patent
Jaafari et al.

(10) Patent No.: US 10,428,111 B2
(45) Date of Patent: Oct. 1, 2019

(54) CANCER TARGETING BY ANTI-EGFR PEPTIDES AND APPLICATIONS THEREOF

(71) Applicants: Mahmoud Reza Jaafari, Mashhad (IR); Masoumeh Zahmatkeshan, Fasa (IR); Seyed Mahdi Rezayat Sorkhabadi, Tehran (IR)

(72) Inventors: Mahmoud Reza Jaafari, Mashhad (IR); Masoumeh Zahmatkeshan, Fasa (IR); Seyed Mahdi Rezayat Sorkhabadi, Tehran (IR)

( * ) Notice: Subject to any disclaimer, the term of this patent is extended or adjusted under 35 U.S.C. 154(b) by 100 days.

(21) Appl. No.: 15/221,832

(22) Filed: Jul. 28, 2016

(65) Prior Publication Data

US 2017/0183380 A1 Jun. 29, 2017

Related U.S. Application Data

(60) Provisional application No. 62/217,877, filed on Sep. 12, 2015.

(51) Int. Cl.

| | |
|---|---|
| *C07K 7/06* | (2006.01) |
| *C07K 7/08* | (2006.01) |
| *A61K 47/60* | (2017.01) |
| *A61K 47/64* | (2017.01) |
| *A61K 47/65* | (2017.01) |
| *A61K 47/69* | (2017.01) |
| *A61K 9/127* | (2006.01) |
| *C07K 14/71* | (2006.01) |
| *C07K 19/00* | (2006.01) |
| *A61K 31/704* | (2006.01) |

(52) U.S. Cl.
CPC .............. *C07K 7/08* (2013.01); *A61K 9/1271* (2013.01); *A61K 9/1275* (2013.01); *A61K 31/704* (2013.01); *A61K 47/60* (2017.08); *A61K 47/64* (2017.08); *A61K 47/65* (2017.08); *A61K 47/6911* (2017.08); *C07K 7/06* (2013.01); *C07K 14/71* (2013.01); *C07K 19/00* (2013.01)

(58) Field of Classification Search
CPC . C07K 7/08; C07K 7/06; C07K 14/71; C07K 19/00; A61K 9/1271; A61K 47/65; A61K 47/60; A61K 47/64; A61K 47/6911
See application file for complete search history.

(56) References Cited

U.S. PATENT DOCUMENTS

| | | | |
|---|---|---|---|
| 7,238,665 B2 | 7/2007 | Wu et al. | |
| 8,834,920 B2 | 9/2014 | Huang et al. | |
| 9,216,228 B2 * | 12/2015 | Kratz | A61K 47/48238 |
| 2011/0200527 A1 | 8/2011 | Xu et al. | |
| 2012/0142606 A1 | 6/2012 | Schmidt-Wolf | |

OTHER PUBLICATIONS

Gyongyossy-Issa et al., The Covalent Coupling of Arg-Gly-Asp-Containing Peptides to Liposomes: Purification and Biochemical Function of the Lipopeptide. Arch Biochem Biophys. May 1, 1998;353(1):101-108.*

De-Kuan Chang, Peptide-Mediated Liposomal Doxorubicin Enhances Drug Delivery Efficiency and Therapeutic Efficacy in Animal Models, PloS one, Dec. 27, 2013, vol. 8, Issue 12.

* cited by examiner

*Primary Examiner* — Ruixiang Li
(74) *Attorney, Agent, or Firm* — NovoTechIP International PLLC

(57) ABSTRACT

A molecule comprising a lipid, a peptide and a linker to bind the lipid to the peptide which have specific amino acid sequence to bind to Epidermal Growth Factor Receptor (EGFR) of tumor cells, and a liposomal composition which is targeted by the molecule, and method for preparing thereof is disclosed.

15 Claims, 27 Drawing Sheets

Specification includes a Sequence Listing.

SEQUENCE LISTING

<160> NUMBER OF SEQ ID NOS: 27

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide binidng EGFR

<400> SEQUENCE: 1

Leu Thr Val Ser Pro Trp Tyr
1               5

<210> SEQ ID NO 2
<211> LENGTH: 14
<212> TYPE: PRT
<213> ORGANISM: Artificial Sequence
<220> FEATURE:
<223> OTHER INFORMATION: Synthetic peptide binding EGFR

<400> SEQUENCE: 2

Met Tyr Trp Gly Asp Ser His Trp Leu Gln Tyr Trp Tyr Glu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide binding EGFR

<400> SEQUENCE: 3

Phe Cys Asp Gly Phe Tyr Ala Cys Tyr Ala Asp Val
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide binding EGFR

<400> SEQUENCE: 4

Ile His Asn Arg Tyr Asn Arg Phe Phe Tyr Trp Tyr
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide binding EGFR

<400> SEQUENCE: 5

Pro Arg Trp Gly Asp Ser His Trp Leu Gln Tyr Trp Tyr Glu
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic peptide binding EGFR

<400> SEQUENCE: 6

Leu Met Trp Gly Gly Ser His Trp Leu Glu Tyr Trp Tyr Glu
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide binding EGFR

<400> SEQUENCE: 7

Gly His Trp Gly Asp Gln His Trp Leu Gln Tyr Trp Tyr Glu
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Synthetic peptide binding EGFR

<400> SEQUENCE: 8

Gly Trp Trp Gly Asp Ser His Trp Leu Gln Tyr Trp Tyr Glu
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide binding EGFR

<400> SEQUENCE: 9

Leu Thr Val Glu Pro Trp Leu
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic spacer peptide

<400> SEQUENCE: 10

Cys Gly Gly Gly
1

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide binding EGFR

<400> SEQUENCE: 11

Leu Thr Val Ser Pro Leu Trp Asp
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide binding EGFR

<400> SEQUENCE: 12

Leu Thr Val Thr Pro Trp Leu
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide binding EGFR

<400> SEQUENCE: 13

Leu Thr Val Gln Pro Trp Pro
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide binding EGFR

<400> SEQUENCE: 14

Leu Thr Val Ser Pro Trp Thr
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide binding EGFR

<400> SEQUENCE: 15

Val Leu Thr Val Gln Pro Trp
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide binding EGFR

<400> SEQUENCE: 16

Leu Thr Val Ser Leu Trp Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide binding EGFR

<400> SEQUENCE: 17

Pro Gly Val Ile Pro Trp Asn
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide binding EGFR

<400> SEQUENCE: 18

Leu Thr Tyr Gln Thr Trp Pro
1               5

```
<210> SEQ ID NO 19
<211> LENGTH: 6
<212> TYPE: PRT
<213> ORGANISM: Artificial Sequence
<220> FEATURE:
<223> OTHER INFORMATION: Synthetic peptide binding EGFR

<400> SEQUENCE: 19

Glu Leu Tyr Val Ser Arg
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide binding EGFR

<400> SEQUENCE: 20

Lys Cys Cys Tyr Ser Leu
1               5

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide binding EGFR

<400> SEQUENCE: 21

Phe Cys Asp Gly Phe Tyr Ala Cys Tyr Lys Asp Ala His Asn Pro
1               5                   10                  15

<210> SEQ ID NO 22
<211> LENGTH: 13
<212> TYPE: PRT
<213> ORGANISM: Artificial Sequence
<220> FEATURE:
<223> OTHER INFORMATION: Synthetic peptide binding EGFR

<400> SEQUENCE: 22

Cys Pro Gly Pro Glu Gly Ala Gly Cys Pro Glu Gly Ala
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Synthetic peptide binding EGFR

<400> SEQUENCE: 23

Cys Arg Glu Lys Ala
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide binding EGFR

<400> SEQUENCE: 24

Met Ala Arg Ser Gly Leu
1               5

<210> SEQ ID NO 25
```

```
<211> LENGTH: 6
<212> TYPE: PRT
<213> ORGANISM: Artificial Sequence
<220> FEATURE:
<223> OTHER INFORMATION: Synthetic peptide binding EGFR

<400> SEQUENCE: 25

Met Ala Arg Ala Lys Glu
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide binding EGFR

<400> SEQUENCE: 26

Met Ser Arg Thr Met Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide binding EGFR

<400> SEQUENCE: 27

Cys Pro Gly Pro Glu Gly Ala Gly Cys
1               5
```

CANCER TARGETING BY ANTI-EGFR PEPTIDES AND APPLICATIONS THEREOF

CROSS REFERENCE TO RELATED DISCLOSURE

This disclosure claims the benefit of priority from U.S. Provisional Patent Disclosure Ser. No. 62/217,877, filed on Sep. 12, 2015, and entitled "CANCER-TARGETED PEPTIDES AND APPLICATION THEREOF" which is incorporated by reference herein in its entirety.

TECHNICAL FIELD

The present disclosure generally relates to poly ethylene glycol and phospholipid conjugated molecules, more particularly to a method for synthesizing poly ethylene glycol-phospholipid conjugated molecules, which can possess cytotoxic effects among other potential effects and activities.

BACKGROUND

One of the major causes of death in the world is cancer. It is estimated that cancer will potentially lead to 12 million deaths in 2030. Chemotherapeutics are widely used in cancer therapy, but their efficacies are often undermined due to their serious side effects.

The improvement of targeted therapeutics against cancer, with enhanced discrimination between tumor cells and non-cancerous counterparts, is one of the major objectives of current anticancer research. Most chemotherapeutic agents do not preferentially accumulate at the tumor sites. Also, toxic side effects can limit dose escalation of current anti-cancer drugs, leading to incomplete tumor response, early disease relapse, and in due course, the development of drug resistance. Targeting via peptide ligands that binds to antigen or Epidermal Growth Factor Receptors (EGFR), is considered as an appropriate approach to improve the selective toxicity of the anticancer therapeutics.

In order to improve the therapeutic indexes of chemotherapeutic agents based on peptide active ingredients, there is a need in the art for the development of new therapeutic agents to specifically deliver drugs to the tumor tissues and selectively act on the target tissue without side effects.

SUMMARY

In one general aspect, the present disclosure describes a molecule including a peptide associated to a lipid via a linker. The molecule is able to bind with an Epidermal Growth Factor Receptor (EGFR) which can be selected from the group consisting of HER1, HER2/neu (or HER2/neu), HER3, or HER4. The peptide used in the molecule can have any of following peptide sequences: LTVSPWY (SEQ ID NO: 1), MYWGDSHWLQYWYE (SEQ ID NO: 2), FCDGFYACYADV (SEQ ID NO: 3), IHNRYNRFFYWY (SEQ ID NO: 4), PRWGDSHWLQYWYE (SEQ ID NO: 5), LMWGGSHWLEYWYE (SEQ ID NO: 6), GHWGDQHWLQYWYE (SEQ ID NO: 7), GWWGDSHWLQYWYE (SEQ ID NO: 8), LTVEPWL (SEQ ID NO: 9), LTVSPLWD (SEQ ID NO: 11), LTVTPWL (SEQ ID NO: 12), LTVQPWP (SEQ ID NO: 13), LTVSPWT (SEQ ID NO: 14), VLTVQPW (SEQ ID NO: 15), LTVSLWT (SEQ ID NO: 16), PGVIPWN (SEQ ID NO: 17), LTYQTWP (SEQ ID NO: 18), and ELYVSR (SEQ ID NO: 19). Additional peptide sequences can be used in the molecule, including KCCYSL (SEQ ID NO: 20), FCDGFYACYKD(AHNP) (SEQ ID NO: 21), CPGPEGAGC(PEGA) (SEQ ID NO: 22), CREKA (SEQ ID NO: 23), pab-MARSGL (SEQ ID NO: 24), pab-MARAKE (SEQ ID NO: 25), pab-MSRTMS (SEQ ID NO: 26), and CPGPEGAGC (SEQ ID NO: 27). In a further general aspect, the present application describes a liposomal composition including a molecule in which a lipid is conjugated to a peptide via a linker. In some implementations, the molar ratio of the peptide to the lipid is in a range of about 1:1 to about 1.5:1.

In one implementation, the peptide used in the molecule may have LTVSPWY (SEQ ID NO: 1) amino acid sequence with a spacer peptide in which 0 to 4 of glycine, proline, cysteine, and in certain cases, 0 to 4 of glycine or/and cysteine, or a mixture thereof are linked.

In one implementation, the peptide may have MYWGDSHWLQYWYE (SEQ ID NO: 2) amino acid sequence with a spacer peptide in which 0 to 4 of glycine, proline, cysteine, more preferably, 0 to 4 of glycine and/or cysteine, or a mixture thereof are linked.

In some implementations, the molecule can include at least one linker between the lipid and the peptide and the linker can contain, for example: polyethylene glycol (PEG). The PEG chains are functionalized to contain reactive groups suitable for coupling with, for example, sulfhydryls, amino groups, and aldehydes or ketones present in a wide variety of ligands. Examples of such PEG-terminal reactive groups include maleimide (for reaction with sulfhydryl groups), N-hydroxysuccinimide (NHS) or NHS-carbonate ester (for reaction with primary amines), hydrazide or hydrazine (for reaction with aldehydes or ketones), iodoacetyl (preferentially reactive with sulfhydryl groups) and dithiopyridine (thiol-reactive), NH2, COOH or combination thereof. The PEG can form several binding such as maleimide-PEG-DSPE, COOH-PEG-DSPE, NHS-PEG-DSPE, NH2-PEG-DSPE, Aldehyde-PEG-DSPE, Ketone-PEG-DSPE, Hydrazon-PEG-DSPE.

In certain cases, the polyethylene glycol can have a molecular weight in a range of about 750 Dalton to about 5000 Dalton.

In some implementations, the lipid phase in the liposomal composition can include at last a phospholipid, cholesterol, and a PEGylated phospholipid.

In another general aspect, a method for preparing a liposomal composition is disclosed. The method can include steps of: reacting a peptide with a lipid to synthesize molecule, synthesizing a liposome; and combining the molecule and the prepared liposome to synthesize a peptide-liposome composition. In some implementations, synthesizing a peptide-liposome composition can be implemented in various methods including: conventional methods, post attachment, and post insertion of the peptide into the liposome.

In some implementations, the method for preparing the liposomal composition can further include loading an active agent to the liposome. In an aspect, the active agent can be selected from a group consisting of cytotoxic/antitumor antibiotics, antimetabolites, anticancer agents, enzymes, detective agents or combination thereof.

In some implementations, about 20 to about 400 peptide ligands can be bound to each liposome surface and in some aspects, liposomes with more ligands on the surface may have more efficiency in tumor treatment.

In some implementations, the lipid phase in the liposome can contain of phospholipid, PEGylated phospholipid, and cholesterol. According to some aspects, the molar ratio of phospholipid:PEGylated phospholipid:cholesterol can be in the range of about 50:30:5 to about 60:40:5.

DETAILED DESCRIPTION

Figure 1A:
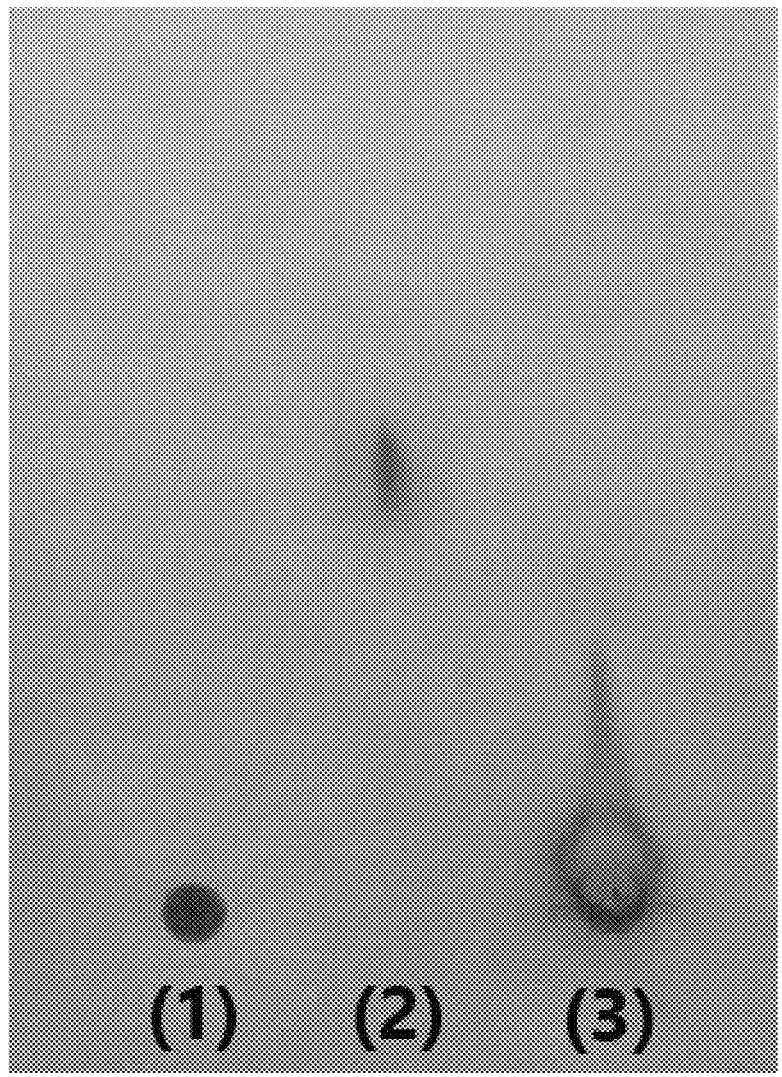
FIG. 1A illustrates a thin layer chromatogram (TLC) of a peptide having LTVSPWY (SEQ ID NO: 1) amino acid sequence (which is donated as 420 W), a Maleimide-PEG-DSPE lipid, and a LTVSPWY (SEQ ID NO: 1) directed micelle.

The following detailed description is presented to enable any person skilled in the art to make and use the teachings of the instant disclosure. For purposes of explanation, specific nomenclature is set forth to provide a thorough understanding of the present disclosure. However, it will be apparent to one skilled in the art that these specific details are not required to practice the teachings of the instant disclosure. Descriptions of specific disclosures are provided only as representative examples. Various modifications to the described implementations will be readily apparent to one skilled in the art, and the general principles defined herein may be applied to other implementations and disclosures without departing from the scope of the present disclosure. The present disclosure is not intended to be limited to the implementations shown, but is to be accorded the widest possible scope consistent with the principles and features disclosed herein.

A molecule is introduced in the present disclosure that is capable, for example, of binding to epidermal growth factor receptor (EGFR) on the surface of human tumor. The molecule can contain at least one peptide and a lipid. The peptides having an amino acid sequence as following can be used in the molecule: LTVSPWY (SEQ ID NO: 1), MYWGDSHWLQYWYE (SEQ ID NO: 2), FCDGFYA-CYADV (SEQ ID NO: 3), IHNRYNRFFYWY (SEQ ID NO: 4), PRWGDSHWLQYWYE (SEQ ID NO: 5), LMWGGSHWLEYWYE (SEQ ID NO: 6), GHWGDQH-WLQYWYE (SEQ ID NO: 7), GWWGDSHWLQYWYE (SEQ ID NO: 8), LTVEPWL (SEQ ID NO: 9), LTVSPLWD (SEQ ID NO: 11), LTVTPWL (SEQ ID NO: 12), LTVQPWP (SEQ ID NO: 13), LTVSPWT (SEQ ID NO: 14), VLTVQPW (SEQ ID NO: 15), LTVSLWT (SEQ ID NO: 16), PGVIPWN (SEQ ID NO: 17), LTYQTWP (SEQ ID NO: 18), and ELYVSR (SEQ ID NO: 19). Additional amino acid sequences of peptides that can be used in the molecule include KCCYSL (SEQ ID NO: 20), FCDGFYA-CYKD (AHNP) (SEQ ID NO: 21), CPGPEGAGC(PEGA) (SEQ ID NO: 22), CREKA (SEQ ID NO: 23), pab-MARSGL (SEQ ID NO: 24), pab-MARAKE (SEQ ID NO: 25), pab-MSRTMS (SEQ ID NO: 26), and CPGPEGAGC (SEQ ID NO: 27). Examples of peptides of the present disclosure include, but are not limited to peptides having the following amino acid sequence: LTVSPWY (SEQ ID NO: 1); MYWGDSHWLQYWYE (SEQ ID NO: 2); and FCDG-FYACYADV (SEQ ID NO: 3). Association of the peptides of the present disclosure with material to be delivered may be covalent or non-covalent and direct or indirect. In some implementations, a peptide of interest in the present disclosure may be covalently attached to a material to be delivered, for example, through a linker.

In some implementations, the peptides of interest of the present disclosure can be conjugated to various compounds, for example, to the distal end of PEG2000-DSPE as lipid phase. Such binding can take place through, for example, Polyethylene Glycol (PEG) as a linker. The PEG chains are functionalized to contain reactive groups suitable for coupling with, for example, sulfhydryl's, amino groups, and aldehydes or ketones present in a wide variety of ligands. Examples of such PEG-terminal reactive groups include maleimide (for reaction with sulfhydryl groups), N-hydroxysuccinimide (NHS) or NHS-carbonate ester (for reaction with primary amines), NH2, COOH or combination thereof, hydrazide or hydrazine (for reaction with aldehydes or ketones), iodoacetyl (preferentially reactive with sulfhydryl groups) and dithiopyridine (thiol-reactive). The PEG can form several binding such as: maleimide-PEG-DSPE, COOH-PEG-DSPE, NHS-PEG-DSPE, NH2-PEG-DSPE, Aldehide-PEG-DSPE, Ketone-PEG-DSPE, Hidrazon-PEG-DSPE.

In some implementations, peptides according to the present application may be attached to nanoparticles. Many varieties of nanoparticles can be used, such as different polymeric and metal nanoparticles, liposomes, solid lipid particles, micelles, quantum dots, dendrimers, microcapsules, lipoproteins, and different nano-assemblies. In some implementations, a number of about 20 to 400 peptide ligands can be bound to each liposome.

The EGFR binding ability of the exemplary peptides used in the present disclosure, retain and as a result mediate specific attachment and uptake of the compounds (e.g., liposomes) by the EGFR cells.

In some implementations, the molecule containing one exemplary peptide, may be associated with any desired material to deliver the material to a desired target cell. Examples of suitable desired materials include, but are not limited to, compounds (e.g., active agents, therapeutic agents etc.), liposomes (e.g., stealth liposomes) and nanoparticles. In one implementation, the molecule can be conjugated to a liposome and the prepared peptide-liposome compositions can be developed with various peptide density on their surface.

In some implementations, the peptides used in the present disclosure can contain spacer peptides. The peptides of interest in the present disclosure can include spacer peptide in which 0 to 5 glycine, cysteine or proline or a mixture thereof linked together. In some implementation, the peptide of interest may contain triglycine (GGG), or/and may contain cysteine-three glycol spacers (CGGG, SEQ ID NO: 10).

Liposomes of the present disclosure can comprise one or more phosphoethanolamine. Suitable examples of phosphoethanolamine that can be used in the practice of this disclosure include, but not limited to 1,2-Distearoyl-sn-glycero-3-phosphoethanolamine (DSPE), 2-Dioleoyl-sn-Glycero-3-Phosphoethanolamine (DOPE), and 1,2-dipalmitoyl-sn-glycero-3-phosphoethanolamine (DPPE).

Liposomes of the present disclosure may also comprise a lipid to which a hydrophilic polymer has been attached, for example, a lipid covalently attached to PEG.

Several liposome-based anticancer drug formulations can be used in this disclosure. For example, Doxil (also known as Caelyx), contains PEG coated liposomes (stealth liposomes) with extended serum half-life and the ability to gradually extravasate through the leaky vasculatures to accumulate in tumors. In addition to such a passive targeting mechanism, active targeting strategies were also proposed, in which antibodies or targeting ligands were used to direct the liposomes to further encourage the interaction between drug loaded liposomes and tumors.

The liposome (which may be a stealth liposome) can comprise an active agent (e.g., therapeutic agent). The active agent that is delivered thorough the prepared compositions of the present disclosure can include any compound desired to be delivered to a specific site in a subject. Any active agent may be used in the practice of the present disclosure, including but not limited to cytotoxic/antitumor antibiotics, antimetabolites, anticancer agents, enzymes, etc. Some of the cytotoxic/antitumor antibiotics can be used in the present disclosures are daunorubicin, doxorubicin (DOX), epirubicin, idarubicin, mitoxantrone, valrubicin, carinomycin, nacetyladriamycin, rubidazone, 5-imidodaunomycin, N30 acetyldaunomycin, and epirubicin. Bleomycin, mitomycin, and actinomycin.

A method is described in the present application for the synthesis of the peptide-liposome, including combination of steps. The steps can include reacting a peptide and a lipid to synthesize a molecule; synthesizing a liposome; combination of the peptide with the lipid to form a peptide-liposome composition. In some implementations, the method for preparing the liposomal composition can further include loading an active agent to the liposome. The active agent can be selected from a group consisting of cytotoxic/antitumor antibiotics, antimetabolites, anticancer agents, enzymes, detective agents or combination thereof. In some implementation, the molecule conjugated to the liposome via post insertion, or post attachment.

Definitions

The terms "peptide-liposome", "targeted liposome", "modified liposome", "post inserted liposome", or "peptid-PEG2000-DSPE" are used interchangeably herein to refer to a liposome that is conjugated to a peptide and that peptide can have, for example, an amino acid sequence of LTVSPWY, or for example, an amino acid sequence of MYWGDSHWLQYWYE (SEQ ID NO: 2). The peptide having LTVSPWY (SEQ ID NO: 1) acid amine sequence, in some charts and tables of the present disclosure, is indicated as 420W, while peptide having MYWGDSHWLQYWYE (SEQ ID NO: 2) amino acid sequence is indicated as 719W.

The term "ligand density," as used herein, means the number of peptide ligands conjugated to the liposome surface.

The following examples represent methods and techniques for carrying out aspects of the present disclosure. It should be understood that numerous modifications can be made without departing from the intended scope of the disclosure.

Example 1: Conjugation of the Peptides to PEG2000-DSPE

LTVSPWY (SEQ ID NO: 1) peptide is used as an exemplary peptide in the present disclosure. The LTVSPWY (SEQ ID NO: 1) peptide (which is denoted as 420W in the figures and tables provided to better describe the present disclosure), is conjugated to Maleimide-PEG2000-DSPE through covalent binding between the thiol group of cysteine residue of peptide and the pyrrole group of maleimide. Peptide was reacted with Maleimide-PEG2000-DSPE in a molar ratio in the range of about 1.2:1 to about 1.5:1 (peptide: maleimide) in a DMSO: chloroform (1:1 molar ratio) solution and 30 µl triethylamine (TEA) at room temperature for 24 hours. Thin layer chromatography (TLC) was used to confirm the formation of LTVSPWY (SEQ ID NO: 1)-PEG2000-DSPE. A TLC plate (silica gel 60 F254, Merck, USA) was placed in a TLC chamber containing mobile phase composed of chloroform, methanol at 85:15 (v/v). The chamber was saturated with iodine vapor to stain the TLC plate. The conjugation of peptide with PEG2000-DSPE was also ascertained indirectly by determining unconjugated peptide fraction using HPLC. KNAUER smart line HPLC (Berlin, Germany) was equipped with a Nucleosil C18, 5 µm, 150×4.6 mm, 100 A° column (KENAUER) and an UV detector (KENAUER S2600) set at 220 nm. The mobile phases employed were A (water+0.1% TFA) and B (acetonitrile+0.1% TFA).

Conjugation of MYWGDSHWLQYWYE (SEQ ID NO: 2) Peptide to PEG2000-DSPE

MYWGDSHWLQYWYE (SEQ ID NO: 2) peptide, which is one of the peptides of interest (and which is denoted as 719W in the figures and tables provided to better describe the present disclosure), is conjugated to Maleimide-PEG2000-DSPE through covalent binding between the thiol group of cysteine residue of peptide and the pyrrole group of maleimide. The peptide was reacted with Maleimide-PEG2000-DSPE in a molar ratio in a range of, for example, 1:1 to about 1:1.5 (peptide: maleimide) in DMSO: chloroform (1:1) solution and 30 µl triethylamine (TEA) at room temperature for 24 hours. Thin layer chromatography (TLC) is used to confirm the formation of 719W-PEG2000-DSPE. A TLC plate (silica gel 60 F254, Merck, USA) was placed in a TLC chamber containing mobile phase composed of chloroform, methanol at 85:15 (v/v). The chamber was saturated with iodine vapor to stain the TLC plate. The conjugation of peptide with PEG2000-DSPE was ascertained indirectly by determining unconjugated peptide fraction using HPLC. KNAUER smart line HPLC (Berlin, Germany) is equipped with a Nucleosil C18, 5 µm, 150×4.6 mm, 100 A° column (KENAUER) and an UV detector (KENAUER S2600) set at 220 nano meter (nm) The mobile phases employed were A (water+0.1% TFA) and B (acetonitrile+0.1% TFA). Elution program was a gradient starting with 100% A and increasing to 25% B in 5 min, 55% B in 10 min and 90% B in 15 min.

Example 2: The Peptide-Liposome Preparation

Liposomes are prepared by the thin lipid film hydration and downsized by sonication and extrusion, and Dox is encapsulated in the liposomes by the remote loading method using ammonium sulfate gradient technique. Briefly, as an example method, HSPC, mPEG2000-DSPE, Mal-PEG2000-DSPE, and cholesterol are mixed in a glass tube from their stock chloroform solutions in molar ratios of about 56.2:38.3:5. The lipid phase Lipids were dried in a rotary evaporator and the trace of chloroform was evaporated overnight with a freeze-dryer. The lipid film was hydrated in an ammonium sulfate solution (250 mM) at 65° C. under argon, sonicated for 15 min, and then extruded through polycarbonate membranes of 200 nm, 100 nm, and 50 nm, sequentially. In order to remove the free ammonium sulfate and provide the conjugation medium, liposomes were then dialyzed against HEPES 10 mM, pH 6.7. Based on the estimate that about 80,000 phospholipid molecules form one liposome with 100 nm in size, and linking efficacy of 100%, the peptide-liposome compositions with 25, 50, 100, and 200 ligand densities were constructed by post insertion method. MYWGDSHWLQYWYE (SEQ ID NO: 2) and LTVSPWY (SEQ ID NO: 1) as the example peptides were used to prepare the peptide-liposome composition.

Example 3: Characterization of Liposomes

Liposome size and polydispersity index were measured by a Dynamic Light Scattering (DLS) instrument. Phospholipid content of the preparations was measured by a method based on Bartlette phosphate assay. In order to determine DOX concentration, aliquots of preparations were dissolved in acidified isopropyl alcohol below DOX self-quenching concentration, and concentration of DOX was measured spectrofluorometerically (ex: 470 nm/em: 590 nm) using serial dilution of Caelyx® as the standard. To determine Dox encapsulation efficiency, concentrations of DOX were determined before and after the purification. The percent of encapsulated DOX was measured using the following formula: % DOX encapsulated=DOX concentration after purification−DOX concentration before purification×100.

For associating of the peptide of interest and the lipid, the LTVSPWY (SEQ ID NO: 1) and MYWGDSHWLQYWYE (SEQ ID NO: 2) both have GGG or CGGG (SEQ ID NO: 10) amino acid sequence, as a peptide spacer. The peptides of interest were easily conjugated to the Mal-PEG2000-DSPE by forming the thiol-ether bond between the thiol of cysteine residue of spacer and maleimide groups. This thiol-ether bond did not easily hydrolyze in vivo, thus maintaining the stability of LTVSPWY (SEQ ID NO: 1)-PEG2000-DSPE or MYWGDSHWLQYWYE (SEQ ID NO: 2)-PEG2000-DSPE. The PEG2000-DSPE was incorporated into the lipid bilayers of liposomes through a simple incubation process while the particle size of liposome was not significantly changed. The hydrophobic DSPE domain is known to spontaneously incorporate itself into the liposome lipid bilayer upon incubation of the LTVSPWY (SEQ ID NO: 1)-PEG2000-DSPE and/or MYWGDSHWLQYWYE (SEQ ID NO: 2)-PEG2000-DSPE conjugates with pre-formed PEGylated liposome, thereby exposing the peptide ligand from the liposome surface. The preparation of PEGylated peptide-liposome compositions by post-insertion method offers a chance to optimize two separate processes, i.e., the preparation of LTVSPWY (SEQ ID NO: 1)-PEG2000-DSPE or MYWGDSHWLQYWYE (SEQ ID NO: 2)-PEG2000-DSPE and that of the liposomes. Most importantly, the preparation process was conducted under mild condition, and thus the leakage of Dox in the incubation process was negligible.

In the present disclosure, four LTVSPWY (SEQ ID NO: 1)-modified DOX liposomal compositions and four MYWGDSHWLQYWYE (SEQ ID NO: 2) modified DOX liposomal compositions, both bearing different peptide densities, namely 25, 50, 100, and 200 LTVSPWY-liposomes were prepared. These preparations were based on the near 100% linking efficacies and the estimate that about 80,000 phospholipid molecules form on the liposome with 100 nm in size. Various physical properties including the particle size averages, polydispersity index (PDI), and the zeta potential of the prepared LTVSPWY (SEQ ID NO: 1)-liposomes with the intended ligand densities are presented and set forth in TABLE. 1A. The same properties of the MYWGDSHWLQYWYE (SEQ ID NO: 2)-liposomes with the intended ligand densities are presented and set forth in TABLE. 1B. The polydispersity of the liposomal compositions targeted with the peptides of interest was similar, as shown in the TABLE. 1A and TABLE. 1B. The size of the particles is within the optimal size range for optimum extravasation and retention of nano-carriers into the tumor tissue. The encapsulation efficiency of DOX was determined and found to be more than 95%. The level of peptide conjugation did not affect the conjugation efficiency of DOX into the liposomes.

TABLE 1A

Physical properties of the LTVSPWY (SEQ ID NO: 1)-liposome formulations.

| Formulation | Z-average Size (nm) | PDI[a] | Zeta potential (mV) |
| --- | --- | --- | --- |
| Doxil-mimic | 105.5 | 0.145 | −11.1 |
| Post inserted liposome 25 Ligand | 102.4 | 0.141 | −12.2 |
| Post inserted liposome 50 Ligand | 102.3 | 0.114 | −11.6 |
| Post inserted liposome 100 Ligand | 101.9 | 0.105 | −10.2 |
| Post inserted liposome 200 Ligand | 104.2 | 0.134 | −11.3 |

[a]polydispersity index (PDI)

TABLE 1B

Physical properties of the MYWGDSHWLQYWYE (SEQ ID NO: 2)-liposomes formulations.

| Formulation | Z-average Size (nm) | PDI[a] | Zeta potential (mV) |
| --- | --- | --- | --- |
| Doxil-mimic | 99.56 | 0.156 | −20.3 |
| Post inserted liposome 25 Ligand | 99.33 | 0.134 | −18.7 |
| Post inserted liposome 50 Ligand | 100.8 | 0.135 | −20.8 |
| Post inserted liposome 100 Ligand | 98.93 | 0.144 | −19.2 |
| Post inserted liposome 200 Ligand | 96.8 | 0.122 | −20.4 |

[a]polydispersity index (PDI)

Figure 1B:
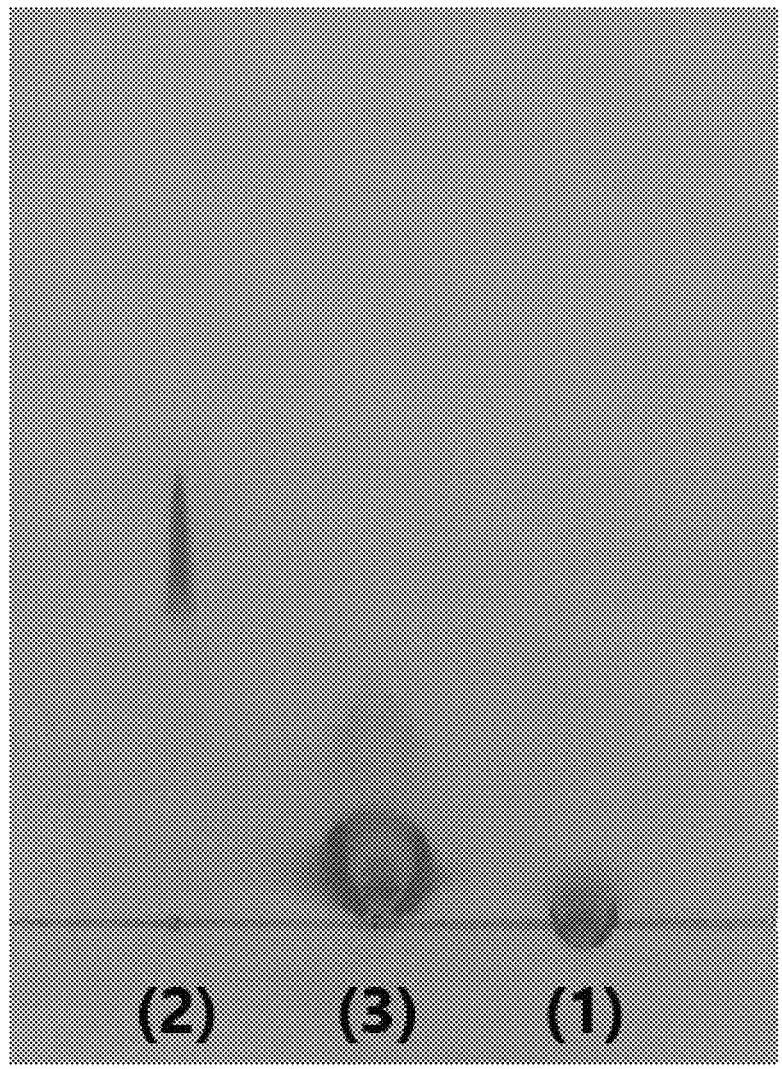
FIG. 1B illustrates a thin layer chromatogram (TLC) of peptide having MYWGDSHWLQYWYE (SEQ ID NO: 2) amino acid sequence (which is donated as 719 W), a Maleimide-PEG-DSPE lipid, and a MYWGDSHWLQYWYE (SEQ ID NO: 2) directed micelle.

Formation of LTVSPWY (SEQ ID NO: 1)-PEG-DSPE and MYWGDSHWLQYWYE (SEQ ID NO: 2)-PEG-DSPE, at the exemplary peptide compositions prepared in this disclosure is confirmed by Thin Layer Chromatography (TLC) as is shown in FIG. 1A and FIG. 1B. In these figures, (1) represents free exemplary peptides (LTVSPWY (SEQ ID NO: 1) peptide in FIG. 1A and MYWGDSHWLQYWYE (SEQ ID NO: 2) in FIG. 1B), (2) denotes the maleimide-PEG-DSPE mixture, and (3) represents the conjugated peptides or the peptide-PEG-DSPE composition. In fact, (3) in these figures denotes the reaction product or in the other word, the liposomal composition targeted with the peptide of interest in the present disclosure (LTVSPWY (SEQ ID NO: 1) peptide in FIG. 1A and/or MYWGDSHWLQYWYE (SEQ ID NO: 2) peptide in FIG. 1B), and maleimide-PEG-DSPE mixture. Since the peptide-PEG-DSPE composition has non-polar characteristics, the changed locations of them are illustrated on the TLC chromatograms. Disappearance of PEG-DSPE spot in the reaction products (which is denoted by (3) in these figures) shows that the reaction was done completely. In other words, Maleimide-PEG-DSPE was entirely reacted with peptide and accordingly the peptide-PEG-DSPE composition was produced.

Figure 1C:
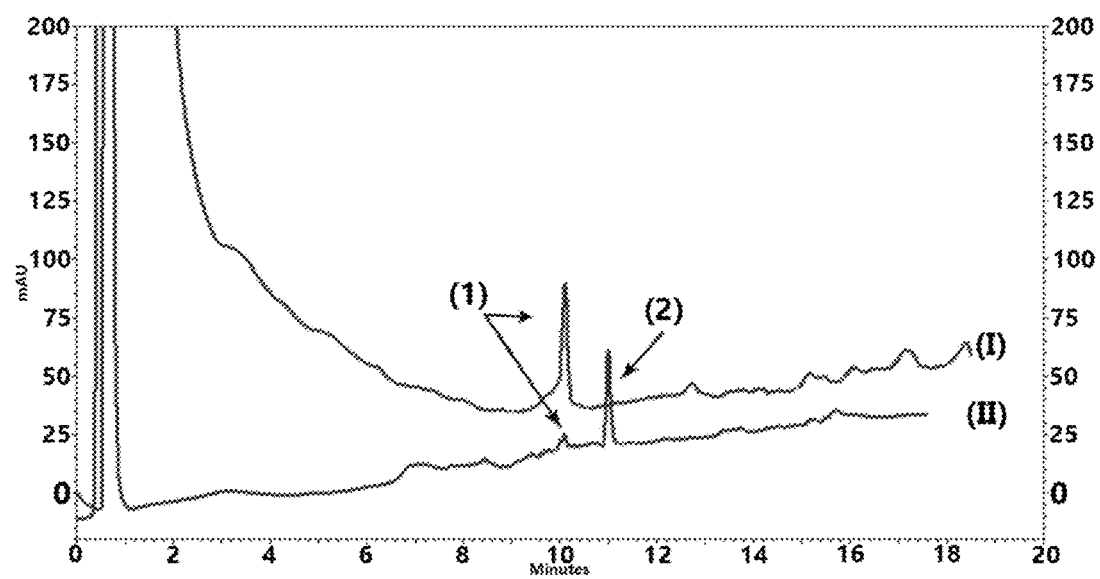
FIG. 1C illustrates a High Pressure Liquid Chromatogram (HPLC) of an example conjugated LTVSPWY (SEQ ID NO: 1) peptide, in which the free peptide extension in the HPLC chromatogram of the conjugated peptide (I) compares with the same in the standard free peptide (II).
Figure 1D:
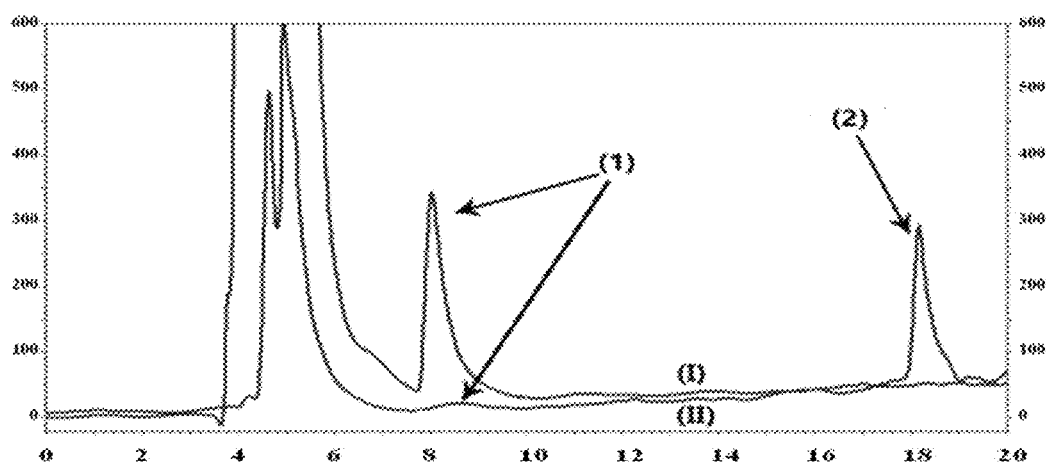
FIG. 1D illustrates a High Pressure Liquid Chromatogram (HPLC) of an exemplar conjugated MYWGDSHWLQYWYE (SEQ ID NO: 2) peptide, in which the free peptide extension in the HPLC chromatogram of the conjugated peptide (I) compares with the same in the standard free peptide (II).

The conjugation of the peptides of interest with the PEG2000-DSPE was ascertained indirectly by determining unconjugated peptide fraction using reversed phase HPLC. The unconjugated exemplary (free) peptides fractions are represented in line (II) and the conjugated peptides are represented in line (I) as illustrated in FIG. 1C and FIG. 1D. Referring now to FIG. 1C, elution program for LTVSPWY (SEQ ID NO: 1) peptide was a gradient starting with 100%, which rises to 10% in 5 min, 75% in 10 min, and 90% in 15 min. The flow rate was set to 1 ml/min in the conducted experiments. In other words, the standard free LTVSPWY (SEQ ID NO: 1) eluted at retention time of 10 min. Under the reaction conditions described, the reaction mixture showed no significant peaks of free peptides. This implied a conjugation efficiency reaching 100% after a 24-hour reaction. In FIG. 1C the standard free peptide eluted with a retention time of ~10 minutes.

Elution program for MYWGDSHWLQYWYE (SEQ ID NO: 2) peptides is illustrated in FIG. 1D. As can be observed in this figure, a gradient starts with 100% and increases to 25% in 5 min, 55% in 10 min, and 90% in 15 min. The flow rate was also set to 1 ml/min in this figure, and standard free peptide eluted with a retention time of ~8 minutes. The differences between (I) and (II) in FIG. 1C and FIG. 1D, are used to determine the post reaction of the peptides of interest and the PEG-DSPE mixtures. Since the peaks in the line (I) and line (II) arise in different times and are not overlapped, this confirms the complete reaction between the peptides and maleimide-PEG-DSPE mixture which is result of reaction between maleamide group in PEG-DSPE and thiol group on peptides.

Figure 2A:
FIG. 2A illustrates the tricine SDS-PAGE of results obtained in connection with Example 8 demonstrating the incorporation of a peptide having LTVSPWY (SEQ ID NO: 1) amino acid sequence, into an example PEGylated liposome, where Lane 1: non-targeted liposome; Lane 2: LTVSPWY (SEQ ID NO: 1), free peptide); lane 3: the peptide after conjugation to Maleimide-PEG2000-DSPE; lane 4: the peptide after incorporation into PEGylated liposome or inserted liposome; and Lane 5: protein marker.
Figure 2B:
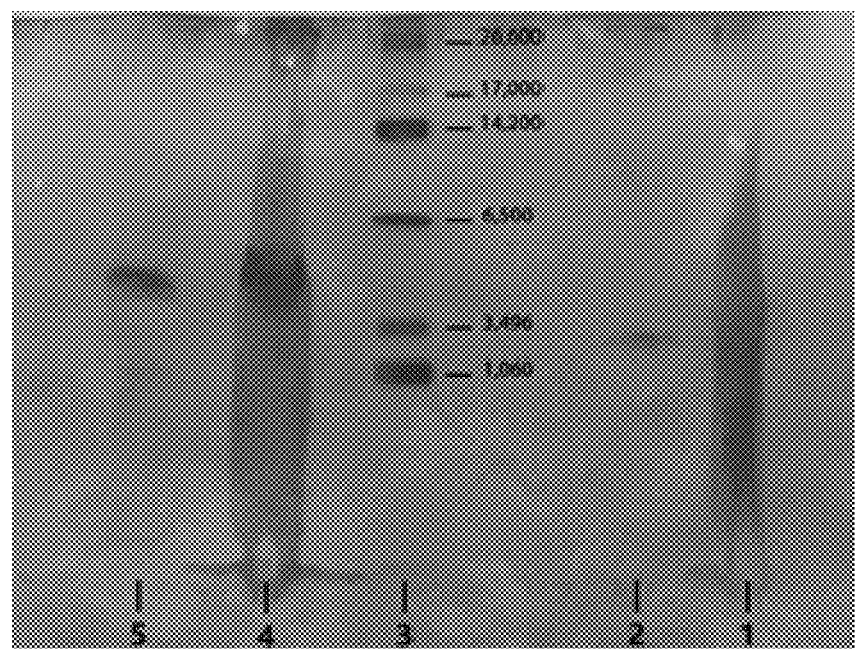
FIG. 2B illustrates the tricine SDS-PAGE of results obtained in Example 8 to confirm incorporation of the peptide having MYWGDSHWLQYWYE (SEQ ID NO: 2) amino acid sequence into the PEGylated liposomes, where Lane 1 is non-targeted liposome; Lane 2: peptide having MYWGDSHWLQYWYE (SEQ ID NO: 2) amino acid sequence; Lane 3: protein marker; Lane 4: peptide after incorporation into PEGylated liposome or inserted liposome; and Lane 5: peptide after conjugation to Maleimide-PEG2000-DSPE.

The conjugation level of the peptides of interest and the exemplar prepared liposomal composition was confirmed by the tricine-SDS-PAGE results, which are illustrated in FIG. 2A and FIG. 2B. Referring to FIG. 2A, this figure shows the migration of the LTVSPWY (SEQ ID NO: 1) peptide to an expected molecular weight of 1.2 kilo Dalton in lane 4. The LTVSPWY(SEQ ID NO: 1)-PEG-DSPE as micelle or liposome, which was run in the adjacent lanes, settled at a molecular weight of 3.2 kDa. The absence of an unligated LTVSPWY (SEQ ID NO: 1) band in lane 3 indicates that the LTVSPWY (SEQ ID NO: 1) was efficiently consumed by the Mal-PEG-DSPE. Moreover, the distinct band at 3.2 KDa in lane 4, which represents the peptide-targeted liposome, verified that LTVSPWY (SEQ ID NO: 1)-PEG-DSPE was efficiently incorporated into the PEGylated liposome in an intact form. In case of using MYWGDSHWLQYWYE (SEQ ID NO: 2) as the second peptide of interest. The MYWGDSHWLQYWYE (SEQ ID NO: 2)-PEG-DSPE as micelle or liposome, was run in the adjacent lanes, settled at a molecular weight of ~4.3 kDa. The absence of an unligated MYWGDSHWLQYWYE (SEQ ID NO: 2) band in lane 5 indicates that the MYWGDSHWLQYWYE (SEQ ID NO: 2) was efficiently consumed by the Mal-PEG-DSPE. Moreover, the distinct band at ~3.2 KDa in lane 4 in FIG. 2A, which represents the LTVSPWY (SEQ ID NO: 1)-targeted liposome, and the distinct band at ~4.3 kDa in lane 4 of FIG. 2B, which represents the MYWGDSHWLQYWYE (SEQ ID NO: 2)-targeted liposome, verified that the LTVSPWY (SEQ ID NO: 1) and the MYWGDSHWLQYWYE (SEQ ID NO: 2) peptides were efficiently incorporated into the PEGylated liposomes in an intact form.

Example 4: Leakage Stability of Liposomes

Leakage stability of the peptide liposomes as well as Caelyx® and Doxil-mimic was assessed using a dialysis method against dexterose 5%. Preparations were transferred briefly to a Slide-A-lyzer dialysis cassettes with 3.5 kD molecular weight cut off (MWCO) and incubated at 37° C. with gentle stirring in a sterile-sealed glass beaker. Aliquots of dialysate were withdrawn at different time points and refreshed with dextrose 5%. Samples were then assayed for the amount of DOX released, and the percentage of DOX that remained encapsulated was then calculated.

Example 5: Liposome-Cell Association Study

SK-BR-3, TUBO, and MDA-MB-231 cells were detached by non-enzymatic cell dissociation solution and $10^5$ cells/well were seeded in 24 well plate. After two overnight incubations (once cell confluence percent reached 80) the medium was replaced with 1 mL FCS free medium containing liposomal preparation at a lipid concentration of 100 nmol phospholipid/mL and incubated at either 37° C. or 4° C. for 3 hours and 6 hours. Cells were then washed three times with PBS and detached by 100 µL of trypsin—EDTA solution and 0.9 mL acidified isopropanol were added to each well and incubated for 30 min at room temperature, then they were incubated overnight at 4° C. to extract the cell-associated DOX. Cell derbies were deposited, and supernatants were then assayed for DOX concentration spectrofluorimetrically. Percentage of DOX associated with cells was then measured.

Example 6: Cytotoxicity Study

The anti-proliferative effects of liposomal preparations containing DOX were assessed using MTT assay. SK-BR-3, TUBO, and MDA-MB-231 cells were seeded at 7000, 10,000, 2500 cells/well in 96 well plates. After an overnight incubation, the medium was replaced with FCS free medium containing 1:2 serial dilutions of liposomal DOX or free DOX. After 3 hours and 6 hours' incubation times at 37° C., cells were washed with pre-warmed complete culture media and re-incubated further for 48 hours at 37° C. in their complete culture medium. Then, the medium was replaced with 100 µL of freshly prepared MTT (10% v/v, 5 mg/mL) and FCS free culture medium. Finally, after 4 hours of incubation at 37° C., the absorbance at 545 nm was recorded. Relative cell death (R) was calculated as follows:

$$R=1-[(A_{test}-A_{blank})/(A_{control}-A_{blank})] \qquad \text{Equation (1)}$$

In the above Equation (1), $A_{test}$ is the absorbance values of the cells treated with the test solutions and $A_{control}$ is the absorbance values of the culture medium (negative control). $A_{blank}$ is the absorbance of MTT solution added in cell free wells. The IC50 was then calculated using CalcuSyn version 2 software (BIOSOFT, UK).

In Vitro Studies

To determine the liposomes uptake by the cells, the densities of the conjugated peptides are measured. FIG. 3A to FIG. 3F represent the data from in the in vitro study. As illustrated in the charts set forth in FIG. 3A to FIG. 3F, the cytotoxicityty of the DOX, unmodified liposomes, and liposomes bearing 25, 50, 100, and 200 ligands of the of the peptides of interest (MYWGDSHWLQYWYE (SEQ ID NO: 2) and/or LTVSPWY (SEQ ID NO: 1) peptides) in SK-BR-3, TUBO, and MDA-MB-231 cells after 3 hours and 6 hours' incubations at 37° C. were investigated and compared. The in vitro uptake units used in this investigation, are nmol liposome phospholipid/$10^5$ cells (mean±SD; n=3 experiments). The sign *** in these figures represents significant differences of peptide-liposomes compared to Caelyx.

Referring further to FIG. 3A to FIG. 3E, the results set forth in these figures, show significant differences in cellular association and/or the uptake of encapsulated DOX in the peptide-liposome compositions compare to Doxil mimic.

Figure 3A:
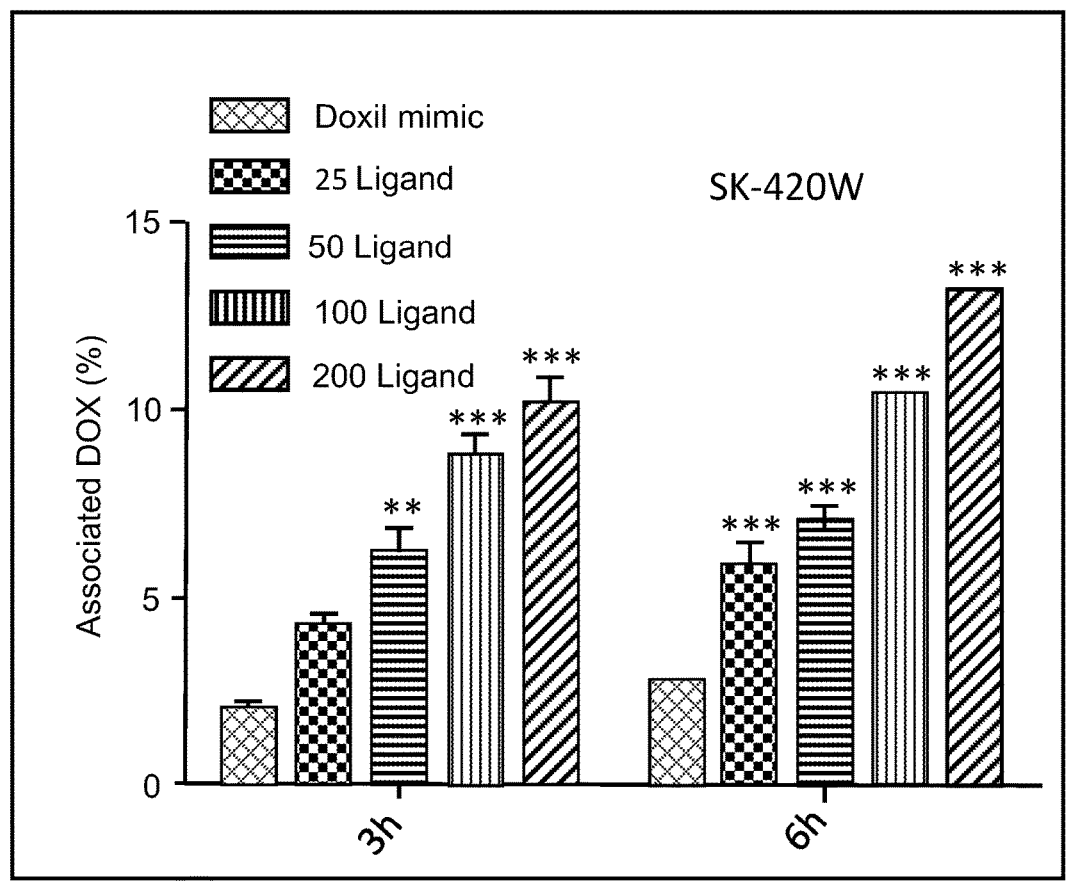
FIG. 3A illustrates in vitro cell uptake of LTVSPWY (SEQ ID NO: 1, 420w)-liposome versus Doxil mimic (the control liposome) in the HER2-overexpressing breast cancer cells (SK-Br-3: human cell line) after 3 and 6 hours exposure times at 37° C.
Figure 3B:
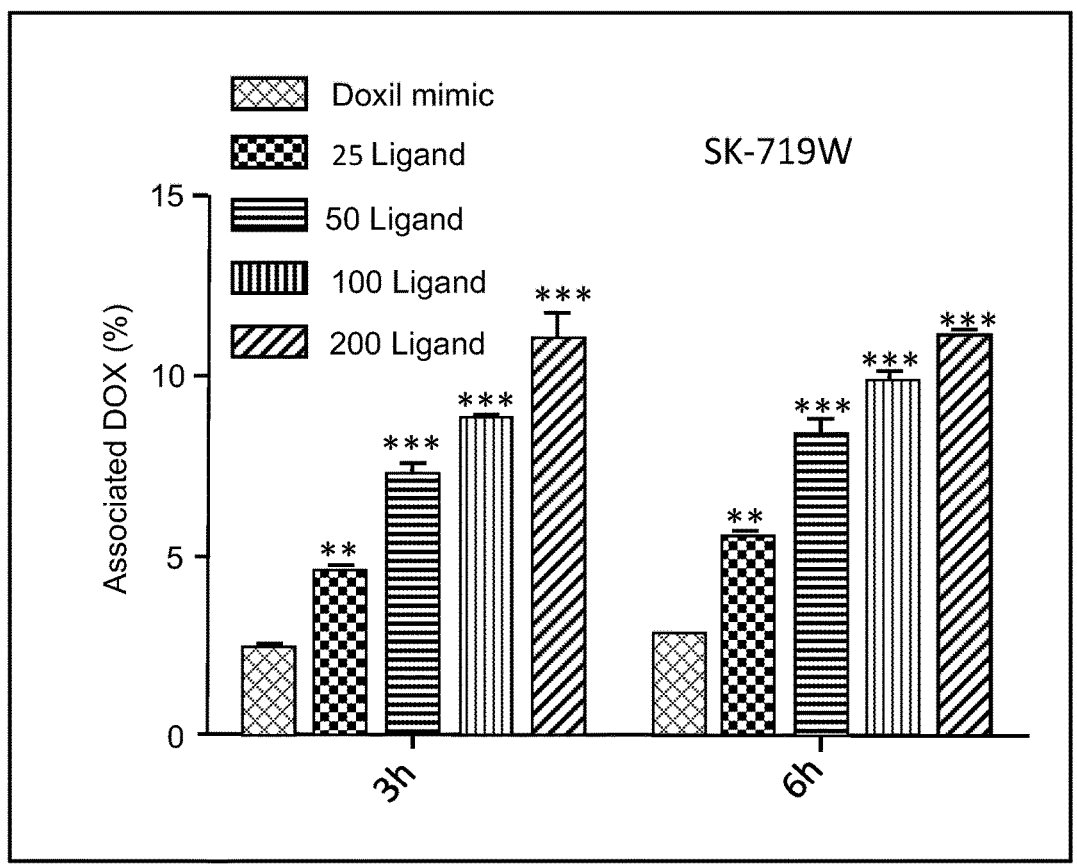
FIG. 3B illustrates in vitro cell uptake of MYWGDSHWLQYWYE (SEQ ID NO: 2, 719W)-liposomes versus Doxil mimic (control liposome) in the HER2-overexpressing breast cancer cells (SK-Br-3: human cell line) after 3 and 6 hours exposure times at 37° C.

The data set forth in these figures, FIGS. 3A and 3B, verify significantly increasing of the cellular association and/or the uptake of encapsulated DOX in HER2 over-expressing breast cancer cells (SK-BR-3) by the increasing the peptide density in all exposure time (P<0.01). Such increasing is the results of multivalency and cooperativity of the liposome's binding that arises via different ligands sharing in binding.

Figure 3C:
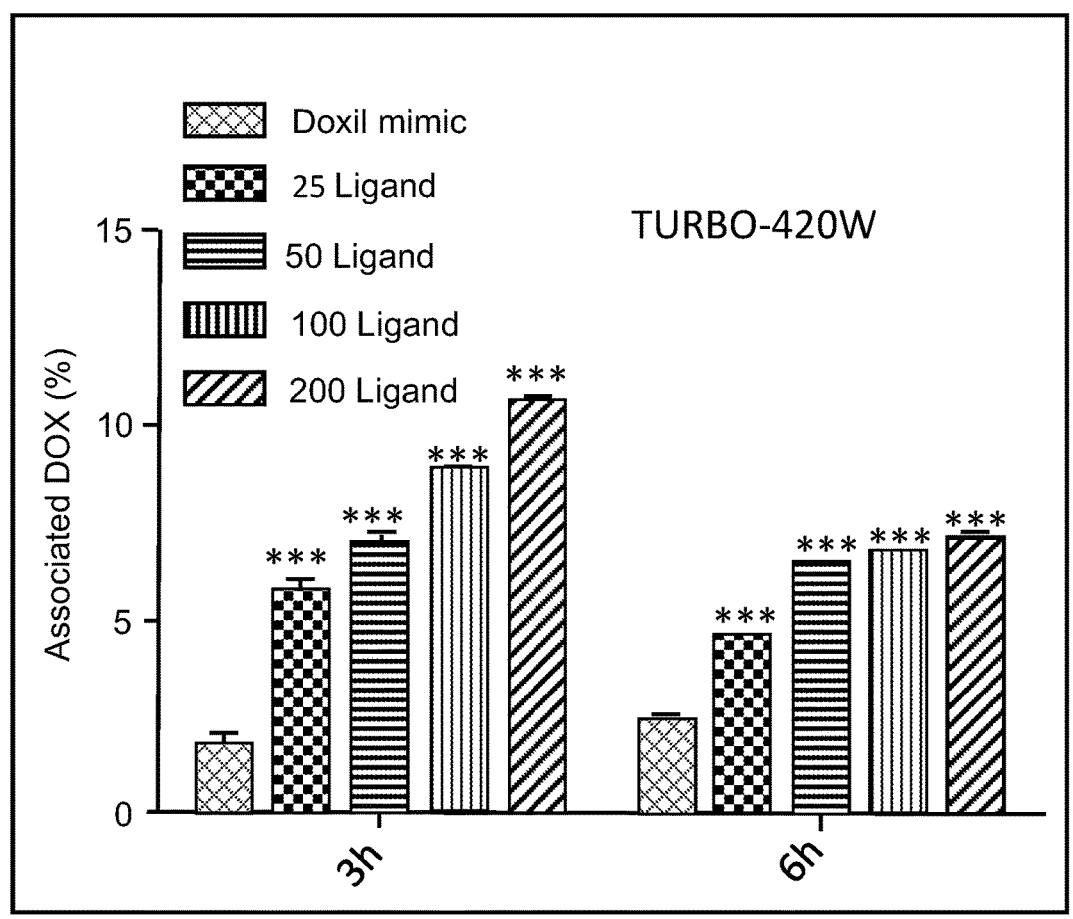
FIG. 3C illustrates in vitro cell uptake of LTVSPWY (SEQ ID NO: 1, 420W)-liposomes versus Doxil mimic (the control liposome) in the TUBO (mice cell line) cells (TUBO-420W) after 3 and 6 hours exposure times at 37° C.
Figure 3D:
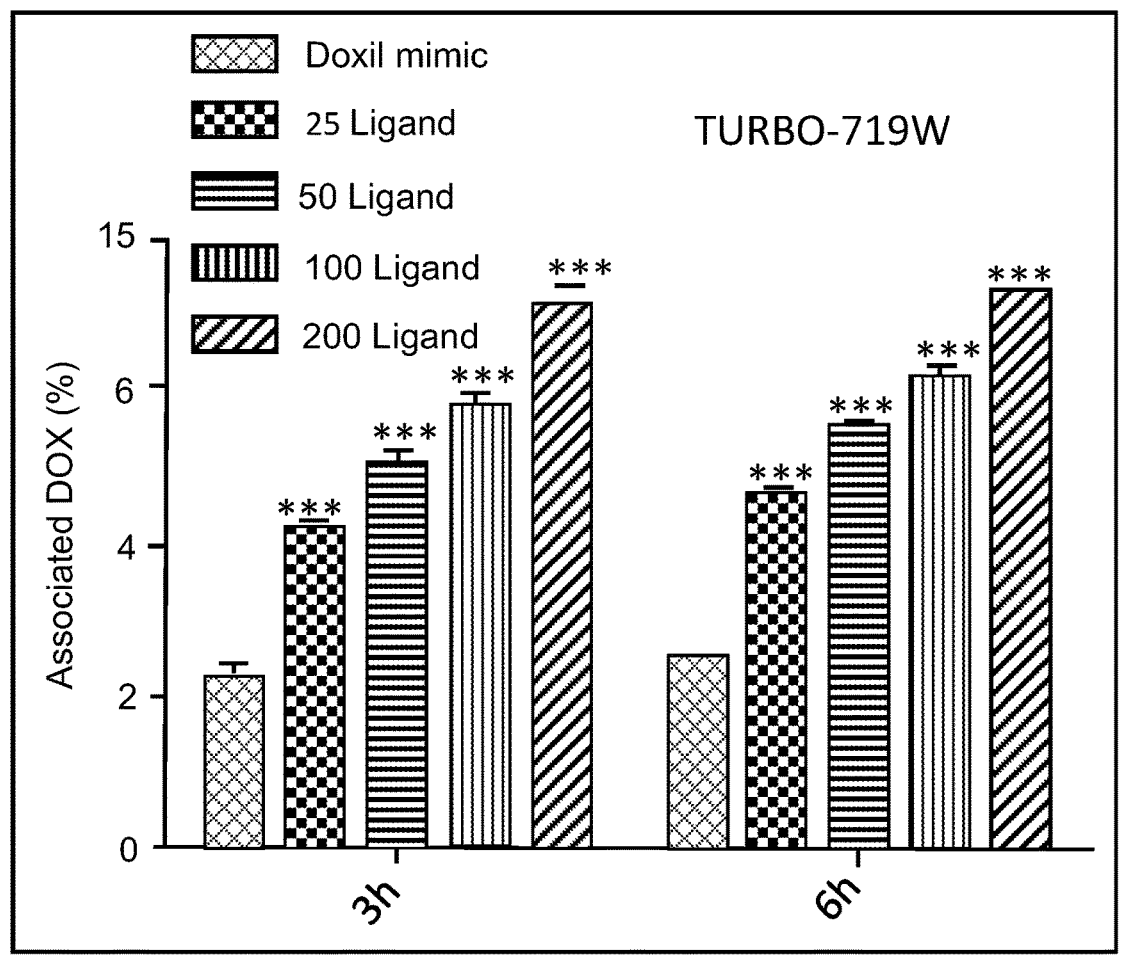
FIG. 3D illustrates in vitro cell uptake of MYWGDSHWLQYWYE (SEQ ID NO: 2, 719W)-liposomes versus Doxil mimic (the control liposome) in the TUBO (mice cell line) cells (TUBO-719W) after 3 and 6 hours exposure times at 37° C.

With reference now to FIG. 3C and FIG. 3D, these figures show the liposome-peptide compositions have significantly higher cellular association and/or the uptake of encapsulated DOX than the plain liposome (Doxil mimic) in all incubation times (P<0.001, ***). Besides, the results presented in these figures indicate that the uptake kinetics are consistent with receptor recycling, which results in gradually enhancement of the formulation uptake during the time.

Figure 3E:
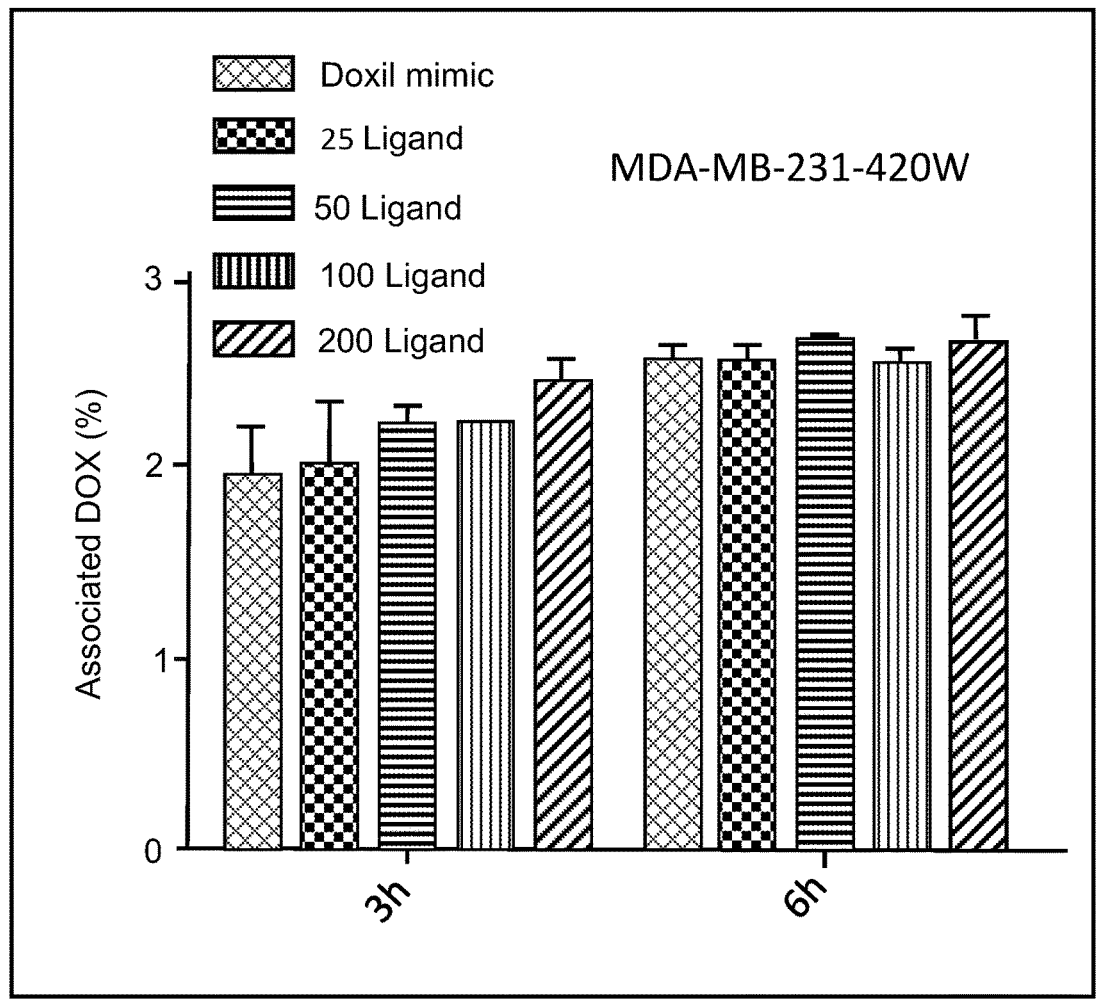
FIG. 3E illustrates in vitro cell uptake of LTVSPWY (SEQ ID NO: 1, 420W)-liposomes versus Doxil mimic (the control liposome) in the HER2-negative breast cancer cells (MDA-MB-231) after 3 and 6 hours exposure times at 37° C.
Figure 3F:
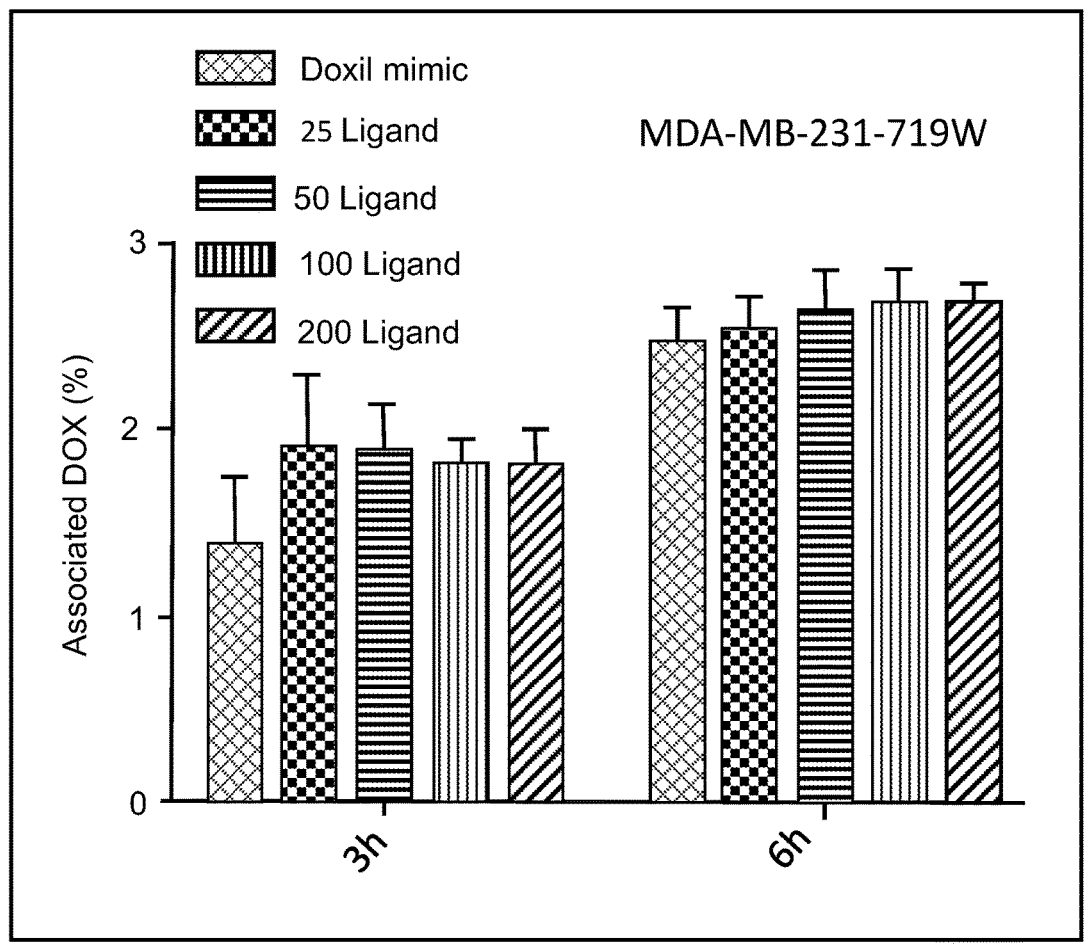
FIG. 3F illustrates the in vitro cell uptake of MYWGDSHWLQYWYE (SEQ ID NO: 2, 719W) liposomes versus Doxil mimic (the control liposome) in the HER2-negative breast cancer cells (MDA-MB-231) after 3 and 6 hours exposure times at 37° C.

However, as represented in FIG. 3E and FIG. 3F, the Peptide-liposome compositions having different ligand densities, did not display significant increases in cellular association and/or the uptake of encapsulated DOX through MDA-MB-231 cells. This finding implies that in the PEGylated targeted liposomes binding specifically to the HER2 receptor, the intracellular delivery of DOX and evading multi-drug resistance can be occurred through the receptor-mediated endocytosis. The results presented and set forth in the FIG. 3A to FIG. 3F further confirm that the targeting property of the exemplar peptides (LTVSPWY (SEQ ID NO: 1) and MYWGDSHWLQYWYE (SEQ ID NO: 2)) did not change after incorporating into the liposome. Moreover, these findings demonstrated that peptide-liposome compositions as efficient target systems can exploit to deliver high levels of DOX into HER2-positive cancer cells.

In Vitro Cytotoxicity Results

The inhibitory concentration data of the 50% (IC50) of free DOX, and the peptide-liposome concentrations against SKBR3 cells, TUBO cells (as HER2-overexpressing cells), and MDA-MB-231 cells (as HER2-Low expressing cells), after 3 h and 6h incubation times are presented and set forth in TABLE. 2A and TABLE. 2B. TABLE 2A present such data when the peptide of interest is LTVSPWY (SEQ ID NO: 1) peptide (which is denoted as 420W in this table) and TABLE. 2B, represents the same data, but when the liposomes are targeted by MYWGDSHWLQYWYE (SEQ ID NO: 2) peptide (which is denoted as 710W in the table). Values in the abovementioned tables are expressed as means±SD (μM, n=3). * P<0.05 differences between IC50 of Doxil mimic and peptide-Doxil. As represented in TABLE 2A and TABLE. 2B, all liposomes modified by the exemplar peptides confirm the higher cytotoxicity (i.e. lower IC50) than untargeted liposomes (DXR and Doxil). Moreover, the higher cytotoxicity is observed in the peptide-liposomes compositions, which have more peptide ligands. This higher cytotoxicity of the 200 peptide ligands in the peptide-liposome compositions compared to lower densities of peptide-liposome composition is attributed to the better binding avidity of the liposome for target receptors as shown in the results of cell uptake studies.

Furthermore, the cytotoxic advantage of the ligand-functionalized formulations can be attributed to the receptor-mediated endocytosis and thus the intracellular delivery of active agent (i.e. drugs). Therefore, increased cellular uptake by increasing ligand density leads to the higher cytotoxicity. In fact, this improved cell uptake and cytotoxicity by increasing ligand density is because of the multivalency and cooperativity of liposome binding that occurs via different ligands sharing in binding. As a result, these properties lead to the higher receptor binding avidity and therefore increased cellular uptake and superior cytotoxicity. The results of cell uptake and cytotoxicity which represented and set forth in FIG. 3A to FIG. 3F and TABLE 2A and TABLE 2B, confirmed this understanding. It is also worth mentioning that, due to the spatial separation afforded by the spacer residue and conjugation on the distal end of PEG moiety, the peptide ligands were able to move without limits and recognized their receptors appropriately. On the other hand, while HER2 has impaired internalization, normally localization of single transmembrane cell surface receptors is efficiently obtained by crosslinking through multivalent ligands. In TABLE 2A and TABLE 2B, the sign *** in these figures represents significant differences of peptide-liposomes compared to Caelyx.

Since the nanoparticles used in the present disclosure are modified with targeting ligands that benefit from endocytosis mediated receptor to entry into the cells, the periods of 3 hours and 6 hours were selected to implement the present investigations. According to art, cell uptake of paclitaxel-loaded PEGylated immunoliposome showed that the PEGylated immunoliposome quickly attached on the surface of the HER2 receptor over-expressing cell lines (BT-474 and SK-BR-3) after 1-hour incubation, and then entered into the cells after 2 hours. Likewise, according to art, the treatment cells with modified liposomes in more periods of time, lead to the extensive cytotoxicity as the results of treatment with modified and unmodified nanoparticles were insignificant and as a results, investigating effects of targeting ligand modification and ligand densities was not obtainable. Furthermore, its cell uptake results showed decreased fluorescent intensity in longer times which is result of toxicity of cells in shorter times. In fact, uptake of modified liposomes containing doxorubicin (DOX) occurs in 3 hours and 6 hours exposure time.

TABLE 2A

Inhibitory concentration 50% (IC50) of free DOX and various LTVSPWY (SEQ ID NO: 1), 420W)-decorated liposomes, against SKBR3, and TUBO as HER2-overexpressing cells and MDA-MB-231 as HER2-Low expressing cells after various incubation times. Values expressed as means ± SD (μM, n = 3).

| 420W Peptide | SKBR3 | | TUBO | | MDA-MB-231 | |
|---|---|---|---|---|---|---|
| | 3 hours | 6 hours | 3 hours | 6 hours | 3 hours | 6 hours |
| DOX | 0.62 ± 0.02 | 0.39 ± 0.05 | 0.15 ± 0.07 | 0.09 ± 0.01 | 0.60 ± 0.05 | 0.26 ± 0.01 |
| Doxil mimc | 28.7 ± 3.5 | 16.5 ± 2.1 | 12.24 ± 0.2 | 6.8 ± 0.3 | 14.1 ± 2.2 | 8.2 ± 0.1 |
| 25 Ligand | 24.9 ± 1.12 | 12.8 ± 0.9* | 11.1 ± 1.22 | 5.5 ± 2.1 | 13.7 ± 1.9 | 8.0 ± 1.6 |

TABLE 2A-continued

Inhibitory concentration 50% (IC50) of free DOX and various LTVSPWY (SEQ ID NO: 1), 420W)-decorated liposomes, against SKBR3, and TUBO as HER2-overexpressing cells and MDA-MB-231 as HER2-Low expressing cells after various incubation times. Values expressed as means ± SD (µM, n = 3).

| 420W Peptide | SKBR3 | | TUBO | | MDA-MB-231 | |
|---|---|---|---|---|---|---|
| | 3 hours | 6 hours | 3 hours | 6 hours | 3 hours | 6 hours |
| Ligand50 | 21.5 ± 0.02** | 10.4 ± 0.05*** | 9.7 ± 0.01** | 4.6 ± 0.05 | 12.6 ± 1.9 | 7.7 ± 0.6 |
| Ligand100 | 17.9 ± 0.09*** | 6.07 ± 0.1*** | 8.08 ± 0.42*** | 3.9 ± 0.21* | 10.5 ± 2.4 | 6.7 ± 1.3 |
| Ligand200 | 15.2 ± 1.12*** | 4.9 ± 0.07*** | 6.5 ± 0.03*** | 2.5 ± 0.12** | 10.2 ± 0.5 | 6.4 ± 0.9 |

*P < 0.05 differences between IC50 of Doxil mimic and peptide-Doxil.
***P < 0.001, differences between IC50 of Doxil mimic and peptide-Doxil.

TABLE 2B

Inhibitory concentration 50% (IC50) of free DOX and different MYWGDSHWLQYWYE (SEQ ID NO: 2) (719W)-decorated liposomes against SKBR3, and TUBO as HER2-overexpressing cells and MDA-MB-231 as HER2-Low expressing cells after various incubation times. Values expressed as means ± SD (µM, n = 3).

| 719W Peptide | SKBR3 | | TUBO | | MDA-MB-231 | |
|---|---|---|---|---|---|---|
| | 3 h | 6 h | 3 h | 6 h | 3 h | 6 h |
| DXR | 0.56 ± 0.02 | 0.24 ± 0.01 | 0.15 ± 0.01 | 0.09 ± 0.03 | 0.60 ± 0.09 | 0.26 ± 0.04 |
| Doxil | 31.94 ± 3.2 | 12.55 ± 2.4 | 12.24 ± 1.22 | 6.8 ± 0.4 | 15.5 ± 3.2 | 8.9 ± 0.7 |
| 25 Ligand | 22.3 ± 4.3 | 7.92 ± 1.21 | 11.95 ± 0.9 | 6.3 ± 0.32 | 15.2 ± 2.9 | 8.7 ± 0.12 |
| Ligand 50 | 20.45 ± 0.1 | 7.07 ± 0.01 | 10.51 ± 0.24 | 5.2 ± 0.05 | 13.7 ± 2.52 | 8.6 ± 0.22 |
| Ligand 100 | 19.07 ± 0.05 | 6.3 ± 0.03 | 8.7 ± 0.01 | 4.2 ± 0.01 | 11.04 ± 3.5 | 8.3 ± 0.51 |
| Ligand 200 | 18.4 ± 0.09 | 4.68 ± 0.12 | 7 ± 0.06 | 2.8 ± 0.02 | 8.7 ± 2.7 | 7.3 ± 1.3 |

*P < 0.05 differences between IC50 of Doxil mimic and peptide-Doxil.

Example 7: Chemotherapy Study

All animal experiments were performed in compliance with the Institutional Ethical Committee and Research Advisory Committee of Mashhad University of Medical Sciences guidelines. Initially, on day 0, female BALB/c mice aged 4-6 weeks were given subcutaneous injections of TUBO tumor cells ($5\times10^5$ cells per mouse) in the right flank. On day 11, post-tumoring mice with palpable tumor received 0.2 mL via a single tail vein injection of either dextrose 5% solution as negative control or doxorubicin encapsulated in liposomes (15 mg/kg). Mice were weighed and tumor sizes were monitored during the experimental period. The tumor volume was estimated by measuring three orthogonal diameters (a, b, and c) with calipers; the volume was calculated as $(a \times b \times c) \times 0.5$ mm$^3$. Tumors that were just palpable were defined as 1 mm$^3$. To survival study, the mice were monitored for up to 120 days post-tumoring or until one of the following conditions for euthanasia was met: (1) their body weight dropped below 20% of their initial mass; (2) their tumor was greater than 2.0 cm across in any dimension; (3) they became lethargic or sick and unable to feed; or (4) they were found dead. The time to reach the endpoint (TTE) for each mouse was calculated from the equation of the line obtained by exponential regression of the tumor growth curve. Subsequently, the percent of tumor growth delay (% TGD) were calculated based on the difference between the mean TTE of treatment group (T) and theme an TTE of the control group (C) (% TGD=[(T−C)/C]×100). Treatment may cause partial regression or complete regression of the tumor in an animal. In a partial regression response, the tumor volume is less than or equal to 50% of its day 1 volume for three consecutive measurements during the course of the study, and greater than or equal to 13.5 mm$^3$ for one or more of these three measurements. In a complete regression response, the tumor volume is less than 13.5 mm$^3$ for three consecutive measurements during the course of the study. An animal with a complete regression response at the end of the study was additionally classified as a tumor-free survivor.

Example 8: Bio-Distribution Study

Two weeks after tumor inoculation, when the tumors were approximately 5 mm wide, mice (3 per group) were injected via the tail vain with either 15 mg/kg of doxorubicin as Caelyx® or targeted liposomes. Control mice received 200 µL of dextrose 5%. Blood samples were collected via retro orbital bleeding (approx. 0.5 mL) 3, 6, and 12 hours after the dosing. After 24 hours, the group was sacrificed for tissue collection. Blood samples were collected by heart puncture, and the whole tumor, kidneys, spleen, heart, lungs as well as a portion of liver and muscle were dissected, weighted and placed in a 2 mL Polypropylene Microvials containing 1 mL of acidified isopropanol and zirconia bead sand homogenized by Mini-Beadbeater-1. The blood was allowed to coagulate at 4° C. and then centrifuged for 10 min at 14,000 rpm. Then, serum was collected and an adequate volume was diluted in 1 mL acidified isopropanol. The homogenized tissue samples and the sera were stored overnight at 4° C. to extract the drug. The samples were then centrifuged and the supernatant was assayed for DOX concentration spectrofluorimetrically (Ex:470 nm, Em:590 nm). The calibration curve was prepared using serial dilutions of Doxil the tissue and sera extracts of the control mice.

In Vivo Studies

In Vivo Therapeutics

Compared to in vitro binding studies, the in vivo environment for binding is much more complex with many anatomical barriers and interference from natural clearance mechanisms such as the reticuloendothelial system (RES) and other nonspecific interactions. Several factors have been identified to influence the pharmacokinetic properties and extravasation behavior of various active targeted liposomes. Immune clearance against the surface conjugated ligands is a major concern. In addition, both surface ligand densities and the length of PEG linkers are also found to be important.

Figure 4A:
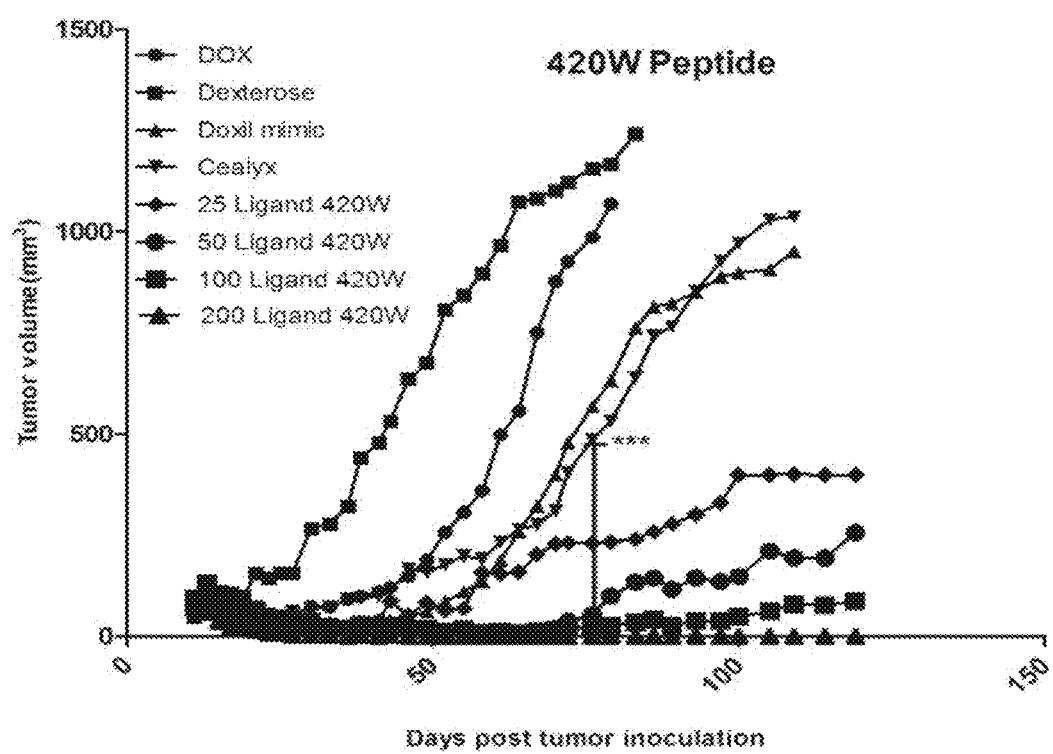
FIG. 4A illustrates the tumor growth rate of non-targeted liposome and LTVSPWY (SEQ ID NO: 1) peptide-liposome compositions (which is denoted as 420W) with different peptide density in female BALB/c mice bearing TUBO breast carcinoma tumor after i.v. administration of a single dose of 15 mg/kg liposomal doxorubicin or dextrose 5% on day 11 after tumor inoculation.
Figure 4B:
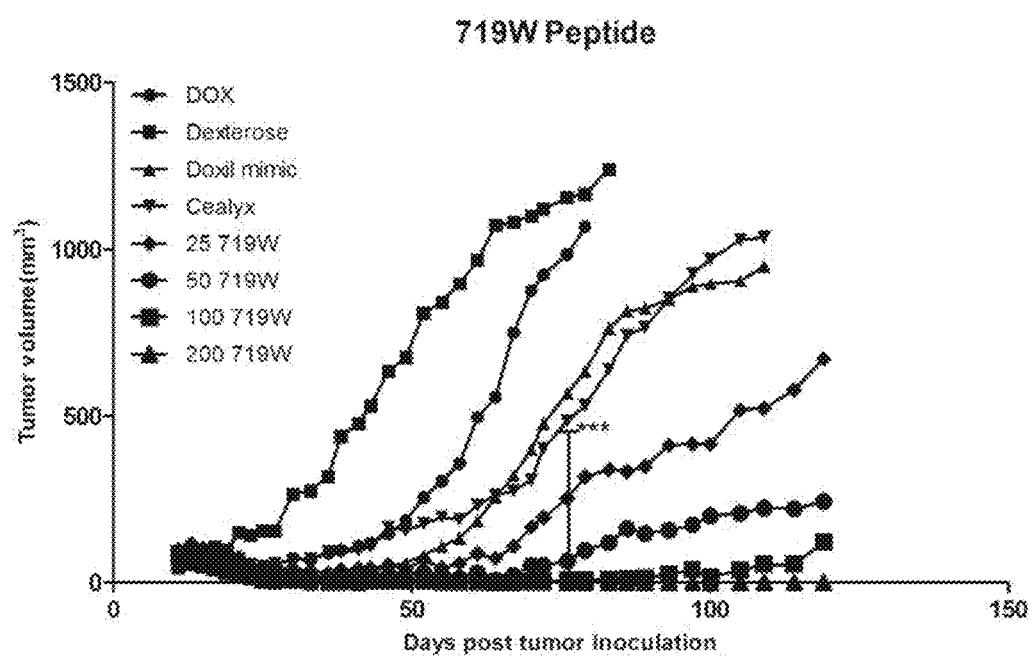
FIG. 4B illustrates the tumor growth rate of non-targeted liposome and MYWGDSHWLQYWYE (SEQ ID NO: 2) peptide-liposomes (719W), with different peptide density in female BALB/c mice bearing TUBO breast carcinoma tumor after i.v. administration of a single dose of 15 mg/kg liposomal doxorubicin or dextrose 5% on day 11 after tumor inoculation.
Figure 4C:
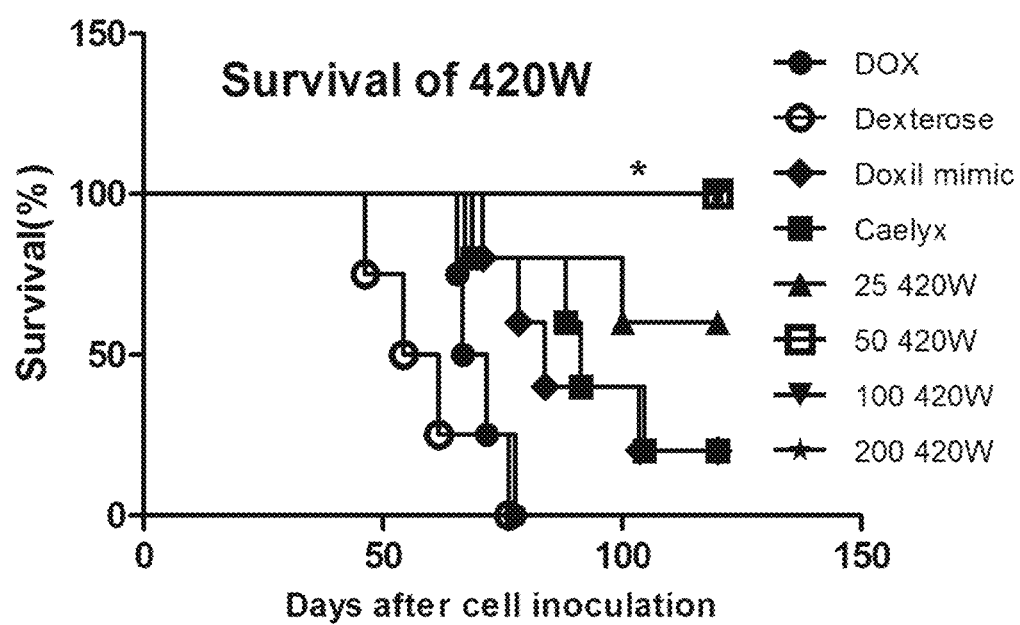
FIG. 4C is the survival curve of non-targeted liposome and LTVSPWY (SEQ ID NO: 1) peptide-liposome composition (420W), with different peptide density in female BALB/c mice bearing TUBO breast carcinoma tumor after i.e. administration of a single dose of 15 mg/kg liposomal doxorubicin or dextrose 5% on day 11 after tumor inoculation.
Figure 4D:
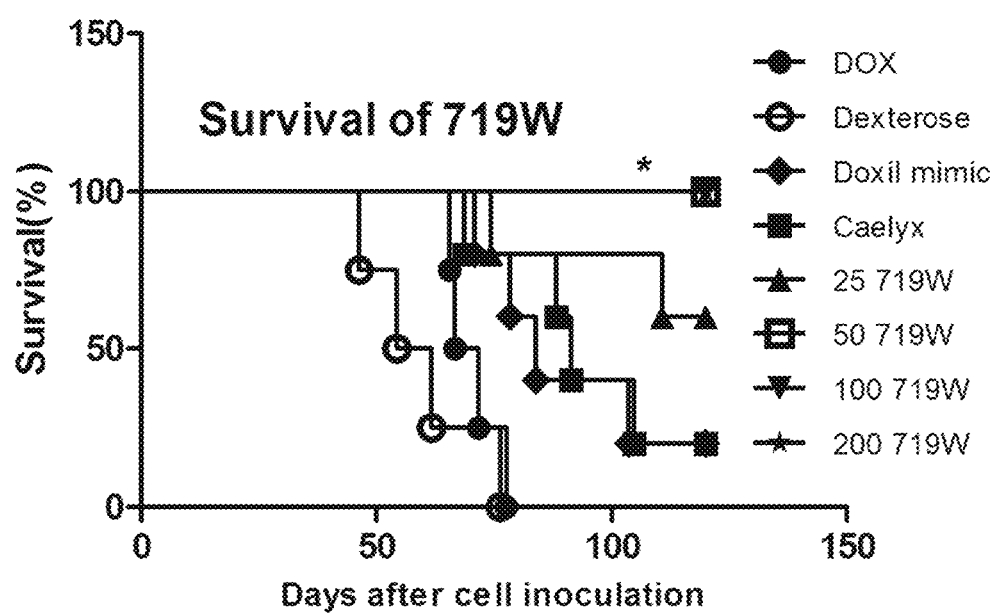
FIG. 4D is the survival curve of non-targeted liposome and MYWGDSHWLQYWYE (SEQ ID NO: 2) peptide-liposome composition (719W), with different peptide density in female BALB/c mice bearing TUBO breast carcinoma tumor after i.v. administration of a single dose of 15 mg/kg liposomal doxorubicin or dextrose 5% on day 11 after tumor inoculation.

Therapeutic efficacy of liposome targeted by the peptides of interest and non-targeted liposome compositions were evaluated in murine TUBO breast carcinoma tumor model. FIG. 4A and FIG. 4C illustrate the results of the in vivo therapeutic efficacy of liposomal composition targeted by LTVSPWY (SEQ ID NO: 1) (which is denoted as 420W). While FIG. 4B and FIG. 4D illustrate the same results when MYWGDSHWLQYWYE (SEQ ID NO: 2) peptide (which is denoted as 719W in the figure) is used for modifying the liposomes. The investigation to get the above-mentioned results took place in female BALB/c mice earing TUBO breast carcinoma tumor after administration of a single dose of 15 mg/kg liposome loaded by doxorubicin (DOX) or dextrose 5% on day 11 after tumor inoculation. In this regard, results of tumor growth rate in terms of mean tumor size (mm$^3$) are presented and set forth in FIGS. 4A and 4B, while FIG. 4C and FIG. 4D illustrate the survival curves and are represented in a Kaplan-Meier plot.

Referring now to FIG. 4A and FIG. 4B, these figures display significant decreasing of the relative tumor volume in both unmodified liposomes and peptide-liposomes in compare to the control group (i.e. dextrose 5% treatment) P<0.0001). In fact, DOX loaded in the exemplar peptide-liposome composition gave a dramatic reduction in tumor size in TUBO tumor-bearing Balb/c mice compared to those treated with untargeted liposomes (P<0.0001). Moreover, decoration of liposomes with the more cancer-specific peptide ligand was expected to introduce higher specificity to the encapsulated DOX for cancer cells. (p<0.05, log rank test).

TUBO tumors responded strongly to 100 ligand LTVSPWY (SEQ ID NO: 1) peptide-liposome (FIG. 4A) and 100 ligand MYWGDSHWLQYWYE (SEQ ID NO: 2) peptide-liposome (FIG. 4B) at 15 mg/kg as DOX. This treatment produced significant antitumor activity with 101% tumor growth delay, 50% complete regression, and 50% tumor free survivor. Tumor growth was significantly delayed in all targeted formulations. Complete tumor regression was observed in all targeted groups. These animals remained tumor-free until the end of the study. This schedule showed significant antitumor activity (P<0.01).

The survival experiment results which are represented in a Kaplan-Meier plot as illustrated in FIG. 4C and FIG. 4D, are used to determine statistical significance in the therapeutic efficacy of targeted and non-targeted liposomal formulations. The survival data indicate that targeting of the liposomes with peptide-Caelyx (either LTVSPWY (SEQ ID NO: 1, 420W) or MYWGDSHWLQYWYE (SEQ ID NO: 2, 719W), at ligand density of 50, 100, and 200, significantly extend mouse survival period in compare to the Caelyx, free doxorubicin (DOX) and dextrose 5%. In general, mice that received unmodified liposomes or the exemplar peptide-liposome composition prepared in this disclosure, tolerated the regimen well. The treatments did not seem to have any obvious adverse impact on the activity level and mean body weight of the treated animals. Analyzing tumor growth curves along with the animal survival results reveal significantly higher effectiveness of all the prepared peptide liposome compositions compared to dextrose 5% (p<0.01). Furthermore, treatment using the peptide-liposome compositions with 50, 100 and 200 ligand densities, displayed stronger tumor inhibition than treatment with other preparations (p<0.0001).

The enhanced therapeutic efficacy of peptide-liposomes compared to unmodified liposomes may be attributed to the capability of the peptides of interest to facilitate the uptake of DOX into the breast cancer cells. The 200 ligand-directed liposomes that provided prolonged retention in tumor tissue (p<0.05), suggesting increased tumor exposure to liposomal drug, and therefore, increased efficacy. Thus, increasing the intracellular DOX concentration and/or improved homing and accumulation of encapsulated DOX in tumor tissue occur by the peptide modified liposomal formulation that is discussed in next section in explanation of bio-distribution of tumor in FIG. 6.

The median survival time (MST), the time to reach the end point (TTE), and the percent of growth tumor delay (% TGD) with dextrose 5%, free DXR, DXL mimic, liposomal DOX bearing 25, 50, 100, and 200 LTVSPWY (SEQ ID NO: 1) peptides (which is denoted as 420W), for each treatment group are presented and set forth in Table 3. A. The same investigations carried out for MYWGDSHWLQYWYE (SEQ ID NO: 2)-liposomes bearing the same ligand densities and the results presented and set forth in TABLE. 3B. Referring now to these tables indicates no significant differences in the MST for dextrose 5% and free DXR. However, all targeted formulations showed significantly increased MST compared to the other formulations (P<0.01). 50, 100, and 200 LTVSPWY (SEQ ID NO: 1) peptide-liposomes showed significantly increased MST compared to non-targeted liposomes. Meanwhile, no significant differences can be observed between targeted formulations.

DOX loaded peptide-liposomes gave a dramatic reduction in tumor size in TUBO tumor-bearing BALB/C mice compared to those treated with untargeted liposomes. Decoration of liposomes with the more cancer-specific ligand was expected to introduce higher specificity to the encapsulated DOX for cancer cells.

The peptide-liposome composition bearing 200 ligand using the peptide of interests resulted in complete tumor remission with no recurrence observed through the completion of the study (day 120) in 100% of animals treated. Log-rank analysis, which compares TTE values of two treatment groups, indicates significant activity for all PLD formulations relative to no treatment (P<0.01). Moreover, peptide-liposome with 50, 100, and 200 ligands exhibited significant survival compare to untargeted liposomes (P<0.01).

Tumor growth was significantly delayed in all targeted formulations. Complete tumor regression was observed in all targeted groups. Typically, these animals remained tumor-free until the end of the investigations. This schedule showed significant antitumor activity (P<0.01).

TABLE 3A

The mean survival times (MST), the time to reach the end point (TTE), and the percent of growth tumor delay (% TGD) with dextrose 5%, free DXR, DXL mimic, liposomal DOX bearing 25, 50, 100, and 200 LTVSPWY (SEQ ID NO: 1) peptides, for each treatment group for mice treated with dextrose.

| 420W | n | MST$^a$ (day) | TTE$^b$ (days) | CR$^c$ | TFS$^d$ | PR$^e$ | TGD$^f$ (%) |
|---|---|---|---|---|---|---|---|
| Dexterose | 4 | 58.05 | 59.7 | 0 | 0 | — | — |
| DOX | 4 | 69.2 | 70.4 | 0 | 0 | — | 18 |
| Cealyx | 5 | 91.4 | 94.6 | 0 | 0 | — | 59 |
| Doxil mimic | 5 | 83.9 | 91.3 | 1 | 1 | — | 53 |
| 25 Ligand | 5 | Undefined | 105.4 | 3 | 2 | — | 76.6 |
| 50 Ligand | 5 | Undefined | 120 | 2 | 2 | — | 101 |
| 100 Ligand | 4 | Undefined | 120 | 2 | 2 | — | 101 |
| 200 Ligand | 5 | Undefined | 120 | 5 | 5 | — | 101 |

$^a$Median survival Time;
$^b$Tumor to reach end point;
$^c$CR: complete regression
$^d$TFS: tumor free survivor;
$^e$PR: partial regression;
$^f$Tumor growth delay

TABLE 3B

The mean survival times (MST), the time to reach the end point (TTE), and the percent of growth tumor delay (% TGD) with dextrose 5%, free DXR, DXL mimic, liposomal DOX bearing 25, 50, 100, and 200 MYWGDSHWLQYWYE (SEQ ID NO: 2) peptides, for each treatment group for mice treated with dextrose.

| 719W | n | Dose (mg/kg) | MST$^a$ (day) | TTE$^b$ (days) | CR$^c$ | TFS$^d$ | PR$^e$ | TGD$^f$ (%) |
|---|---|---|---|---|---|---|---|---|
| Dexterose | 4 | — | 58.05 | 59.7 | 0 | 0 | — | — |
| DOX | 4 | 10 | 69.2 | 70.4 | 0 | 0 | — | 18 |
| Cealyx | 5 | 15 | 91.4 | 94.6 | 0 | 0 | — | 59 |
| Doxil mimic | 5 | 15 | 83.9 | 91.3 | 1 | 1 | — | 53 |
| 25 Ligand | 5 | 15 | Undefined | 109 | 2 | 2 | — | 83 |
| 50 Ligand | 4 | 15 | Undefined | 120 | 2 | 2 | — | 101 |
| 100 Ligand | 5 | 15 | Undefined | 120 | 4 | 4 | — | 101 |
| 200 Ligand | 5 | 15 | Undefined | 120 | 5 | 5 | — | 101 |

$^a$Median survival Time;
$^b$Tumor to reach end point;
$^c$CR: complete regression
$^d$TFS: tumor free survivor;
$^e$PR: partial regression;
$^f$Tumor growth delay

Example 9: Bio-Distribution of the LTVSPWY (SEQ ID NO: 1) Peptide-Liposomes

Figure 5A:
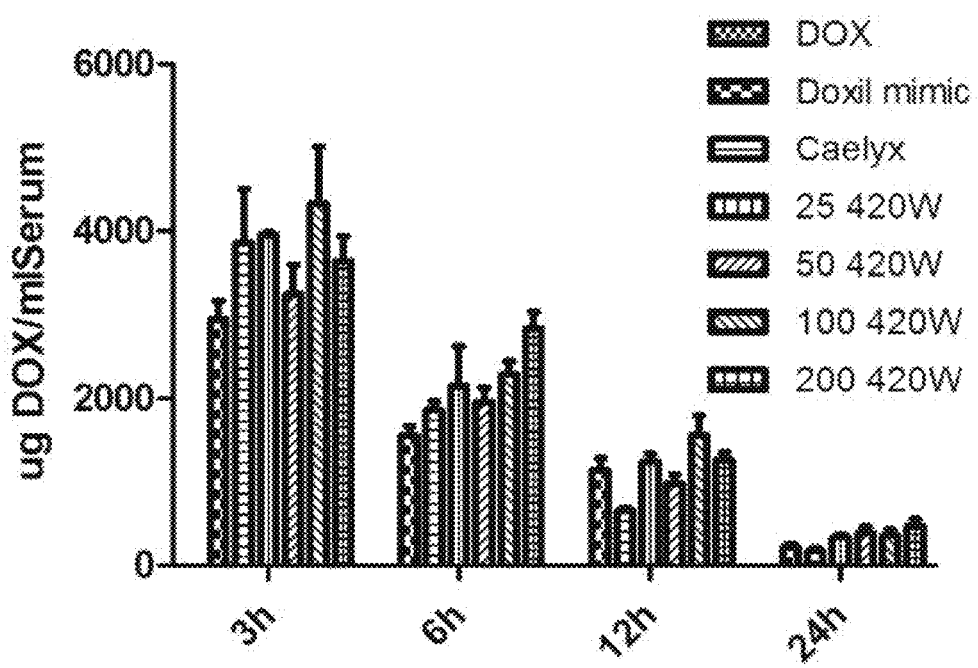
FIG. 5A illustrates the plasma concentration profile of DOX at different time point injection of free drugs, non-targeted liposome and LTVSPWY (SEQ ID NO: 1) peptide-liposome compositions (420W), with various peptide ligand densities, in TUBO-tumor bearing BALB/c mice with a dose of 15 mg/kg as DOX.
Figure 5B:
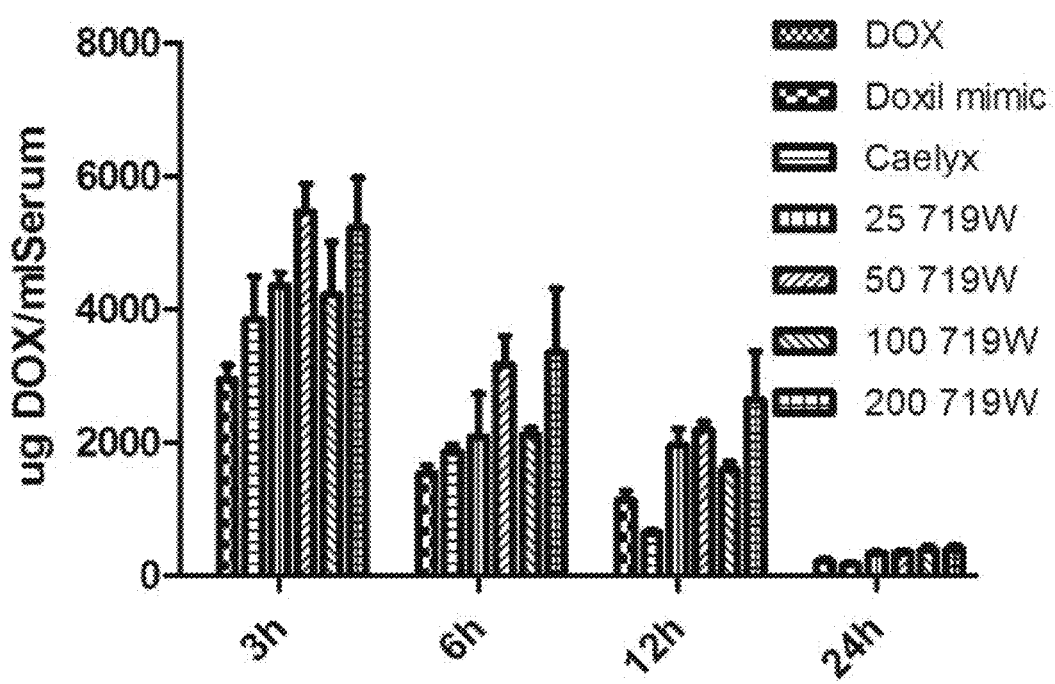
FIG. 5B illustrates the plasma concentration profile of DOX at different time point injection of free drugs, non-targeted liposome and MYWGDSHWLQYWYE (SEQ ID NO: 2) peptide-liposome compositions (719W), with various peptide ligand densities, in TUBO-tumor bearing BALB/c mice with a dose of 15 mg/kg as DOX.
Figure 5C:
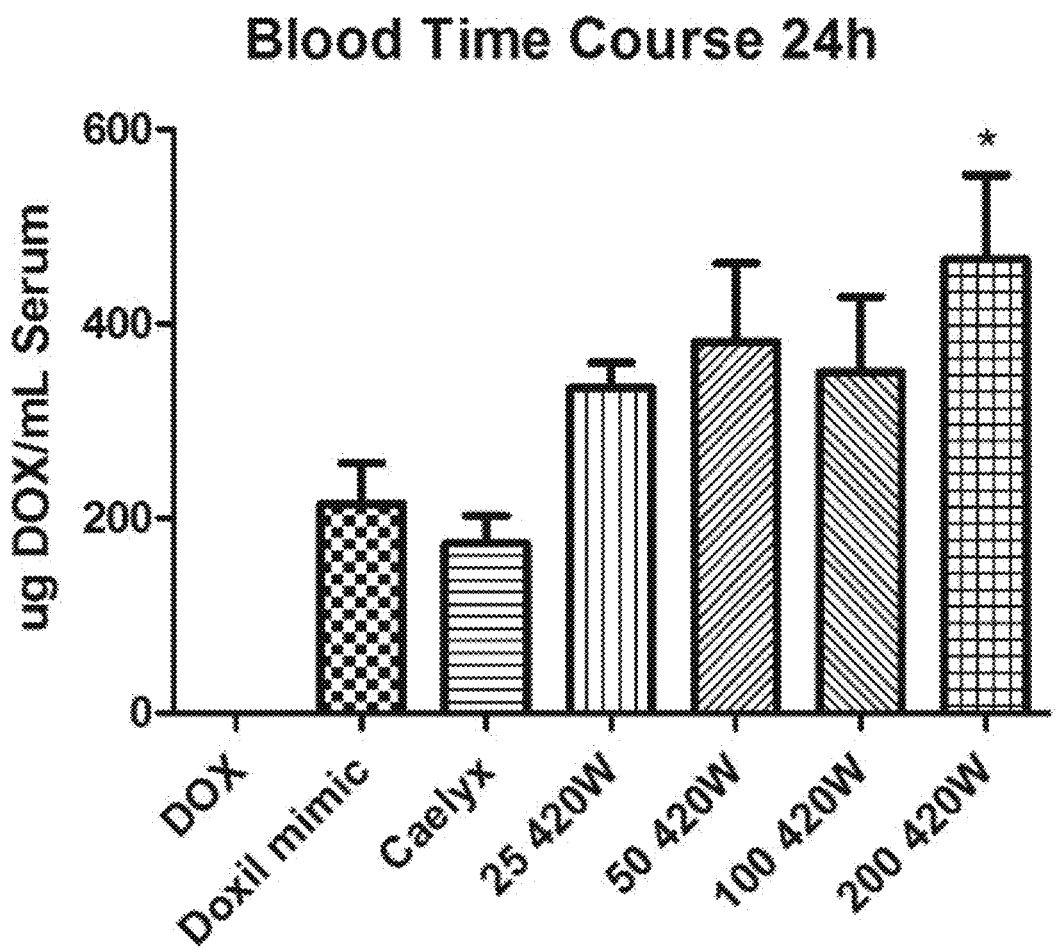
FIG. 5C illustrates the plasma concentration profile of DOX at 24 h after intravenous injection of free drugs, non-targeted liposome and LTVSPWY (SEQ ID NO: 1) peptide-liposome composition (420W), with various peptide ligand densities, in TUBO-tumor bearing BALB/c mice with a dose of 15 mg/kg as DOX.
Figure 5D:
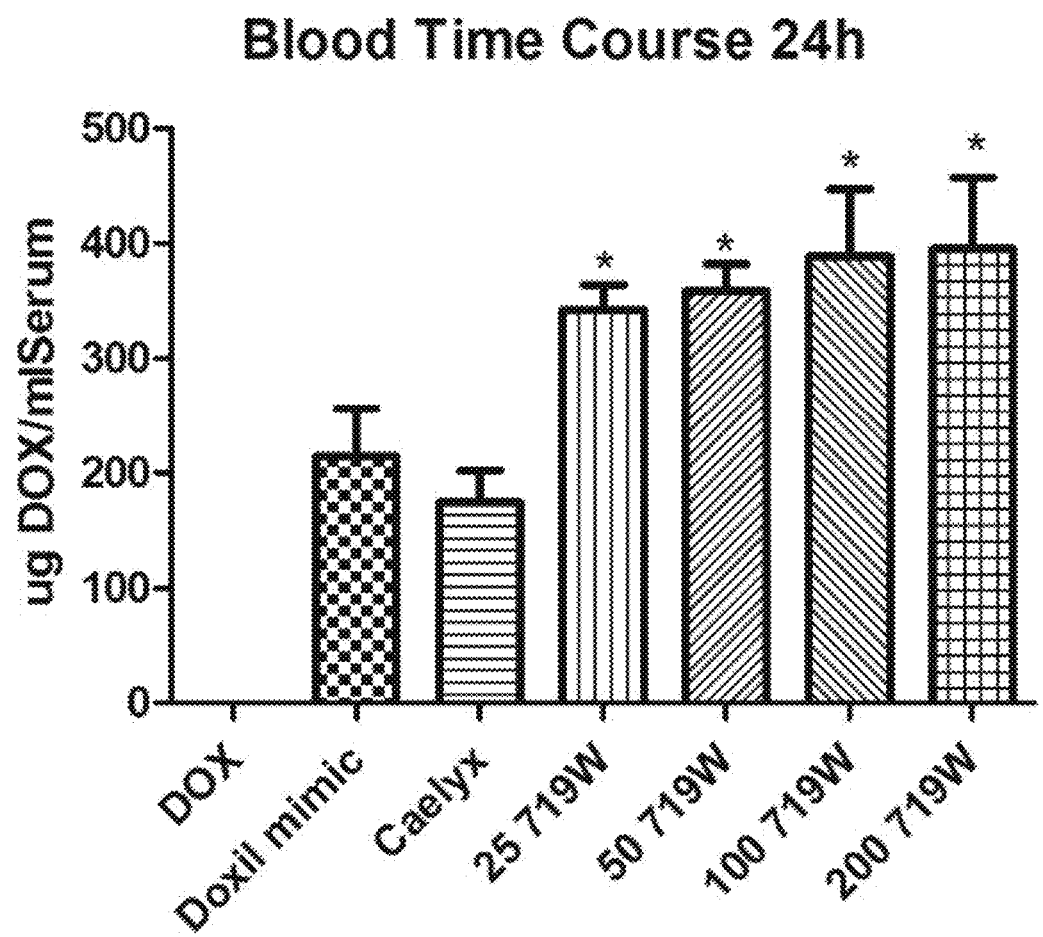
FIG. 5D illustrates the plasma concentration profile of DOX at 24 hours after intravenous injection of free drugs, non-targeted liposome and MYWGDSHWLQYWYE (SEQ ID NO: 2) peptide-liposome composition (719W), with various peptide ligand densities, in TUBO-tumor bearing BALB/c mice with a dose of 15 mg/kg as DOX.
Figure 6:
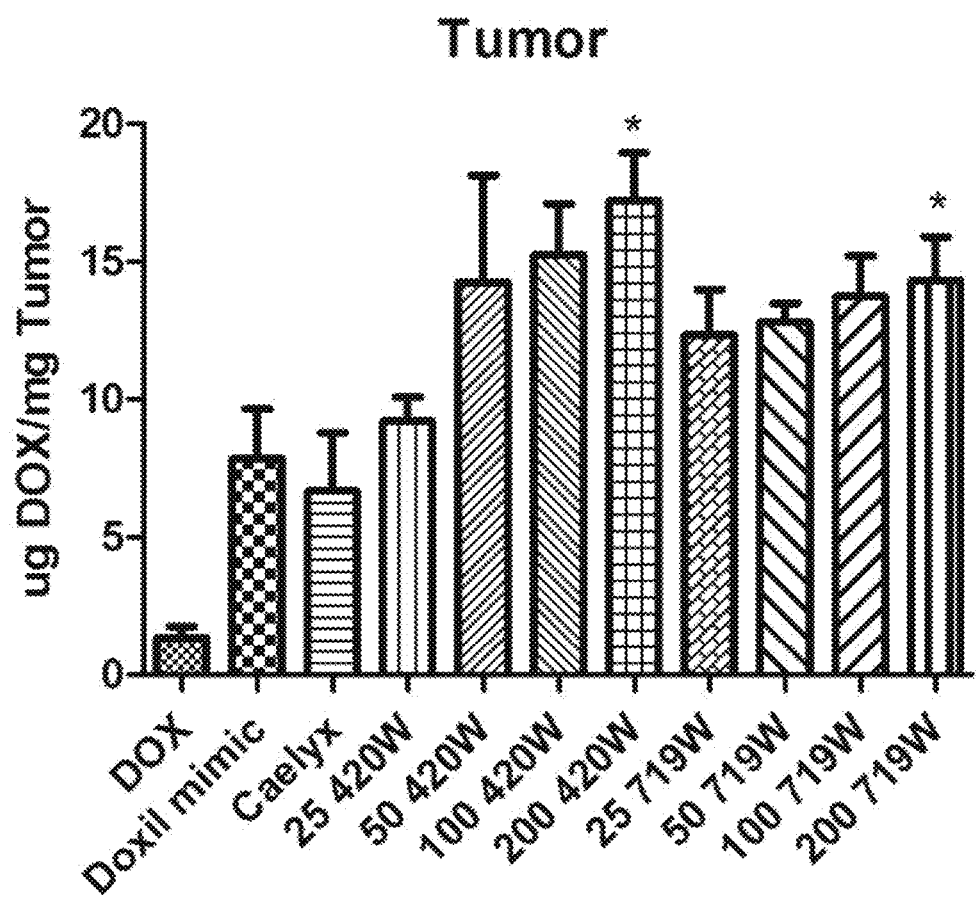
FIG. 6 illustrates the DOX bio-distribution of tumor in TUBO-tumor bearing BALB/c mice at 24 h following i.e. injection with a dose of 15 mg/kg DOX formulations.

To facilitate a comprehensive analysis of liposome bio-distribution, the tissue distribution data of the following organ's tissues are presented separately in FIG. 5 and FIG. 6; blood, liver and spleen (used as an approximation of the Reticuloendothelial system, RES); tumor; and other tissues (consisting of kidneys, heart, lungs and muscle).

Referring now to FIG. 5A and FIG. 5B, these figures illustrate the plasma concentration profiles of DOX, PEGylated liposomes, or PEGylated peptide-liposomes at different time points, in TUBO-tumor bearing BALB/c mice with a dose of 15 mg/kg as DOX. Whilst, FIG. 5C and FIG. 5D illustrate the plasma concentration profiles of DOX, PEGylated liposomes, or PEGylated peptide-liposomes after 24 hours after intravenous injection, in TUBO-tumor bearing BALB/c mice with a dose of 15 mg/kg as DOX. Each data represents as mean±SD (n=3). * in these figures represents the significant differences of peptide-liposomes compared to Caelyx. As data shows encapsulated DOX in both targeted and non-targeted liposomes gradually removed from the circulation.

Referring now to FIG. 5A and FIG. 5B, these figures illustrate DOX was quickly removed after intravenous injection, and was below the detection limit after 3 hours. However, DOX in PEGylated liposome and PEGylated peptide-liposome compositions showed slower elimination from the circulation. The prepared peptide-liposome compositions display a bio-distribution pattern characteristic of long-circulating liposomes, including reduced reticuloendothelial uptake and high blood concentrations. This finding shows that the presence of peptide has no adverse effect on clearance time of peptide-targeted liposomes compared to the non-targeted liposomes, which is the result of small size of peptides as well as their invisibility to immune system. On the other hand, attaching peptide at the distal end of PEG, presence of free PEG, and long-chain PEG molecules, lead to increased circulation behavior of targeted liposomes.

In contrast, besides the applying PEGs of high molecular weights in the targeting system in the present disclosure, the free PEG, which was not linked to the peptide, is beneficial to tumor targeting in vivo due to the long circulation time. Therefore, the comparable long-circulation behavior of peptide-Caelyx and Caelyx could be attributed to the mentioned reasons. These results indicated that the conjugation of peptide to the surface of liposome not only wasn't less than that of non-targeted liposomes but was also significantly more than it at 24 hours' time point (P<0.05 for 200 420W-liposome and 719W-liposome in all ligand density).

Referring now to FIG. 5C and FIG. 5D, it is notable that the presence of LTVSPWY (SEQ ID NO: 1) and MYWGDSHWLQYWYE (SEQ ID NO: 2) peptides on liposomes at different ligand density resulted in higher blood concentration profile at 24 hours' time point compared to plain liposomes.

To shed light on the contribution of DOX tumor accumulation on the therapeutic activity of formulations in the present disclosure, concentration of DOX as part of non-targeted liposomes, the LTVSPWY (SEQ ID NO: 1) peptide and MYWGDSHWLQYWYE (SEQ ID NO: 2) peptide decorated formulation in tumor and major organs was assessed 24 hours after the last injection, as illustrated and described in more detail in charts set forth in FIGS. 5C and 5D, as well as FIG. 6 and FIGS. 7A-7F.

FIG. 6 illustrates the DOX bio-distribution of tumor in TUBO-tumor bearing BALB/c mice at 24 hours following (i.e. injection with a dose of 15 mg/kg DOX formulations) when the used peptide is LTVSPWY (SEQ ID NO: 1). Values expressed as mean±SD (n=3). * in this figure represent significant differences of peptide-liposomes compared to Caelyx. Enhanced accumulation of ligands and targeted-conjugates in tumor has been studied for a long time as a pattern for targeted cancer therapies. Once liposomes and the exemplary peptide-liposomes are localized in tumor, the accumulation of peptide-liposomes in HER2-positive tumors is evaluated and the results are compared to the accumulation results of unmodified formulations. Both anti-HER2 peptide-liposomes and non-targeted liposomes showed efficient localization in breast tumor model. According to FIG. 6, at 24 hours after injection, tumor accumulation of LTVSPWY (SEQ ID NO: 1)-liposome bearing 200 peptide ligands were 2.6-folds greater than the Caelyx (p<0.05). while this occurs for MYWGDSHWLQYWYE (SEQ ID NO: 2)-liposomes bearing 200 ligands were 2.14-folds greater than that of Caelyx® (p<0.05). In fact, the increased tumor accumulation with the significantly greater antitumor efficacy of peptide-liposomes in comparison with non-targeted liposomes confirm the mechanism of high tumor accumulation for therapeutic profit of targeted systems. Moreover, therapeutic value of targeted formulations bearing less peptide density (50 or 100) appeared significantly is higher than the same in plain liposomes in spite of insignificant accumulation in tumor. As a result, targeting the liposomes with the peptides of interest in this disclosure may result in determinant pharmacodynamic changes with improved therapeutic efficacy by changing distribution of DOX from the extracellular to the intracellular compartment of tumor. Therefore, targeting mediated by ligands not only quantitatively enhanced the tumor localization, but also qualitatively changed the delivery mechanism to tumor cells for increased efficacy.

Figure 7A:
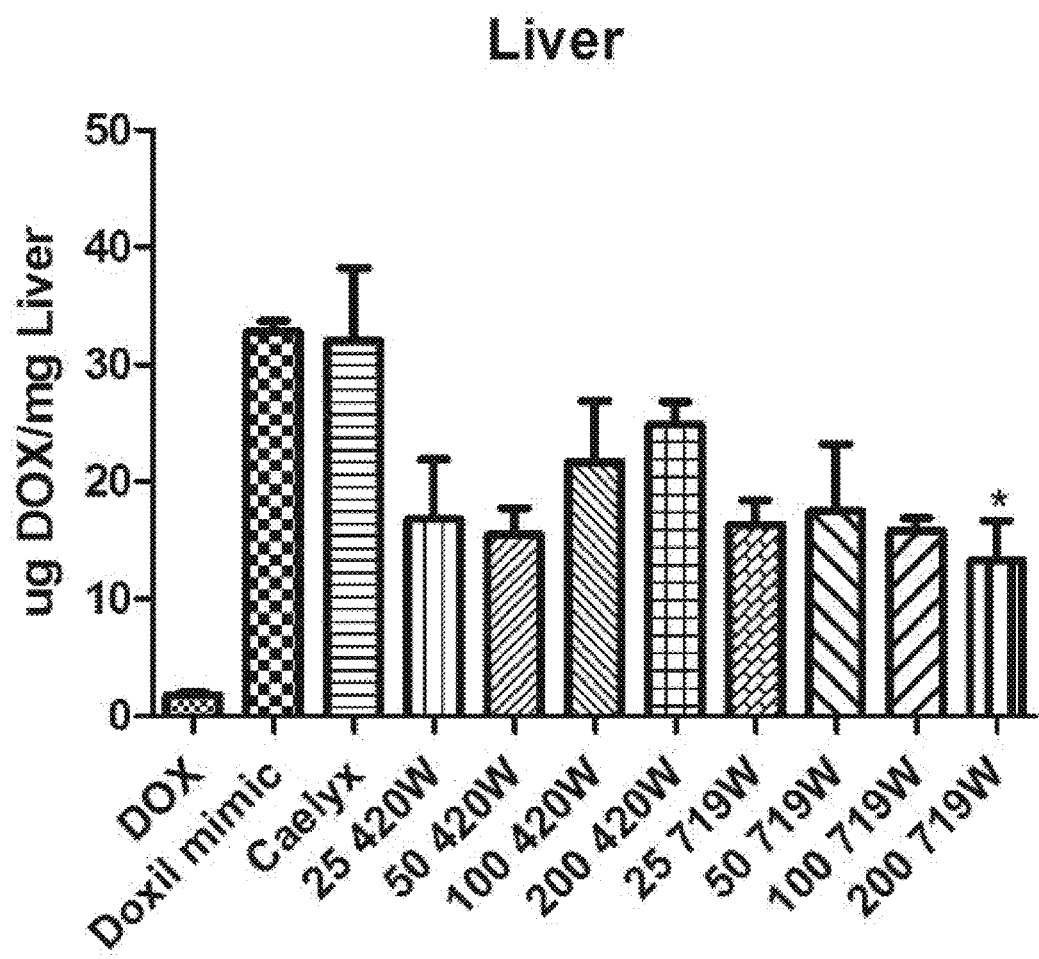
FIG. 7A illustrates the various liposomal composition bio-distribution results in BALB/c mice bearing TUBO tumor treated with a dose intravenous injection of 15 mg/kg liposomal DOX, in the Liver.
Figure 7B:
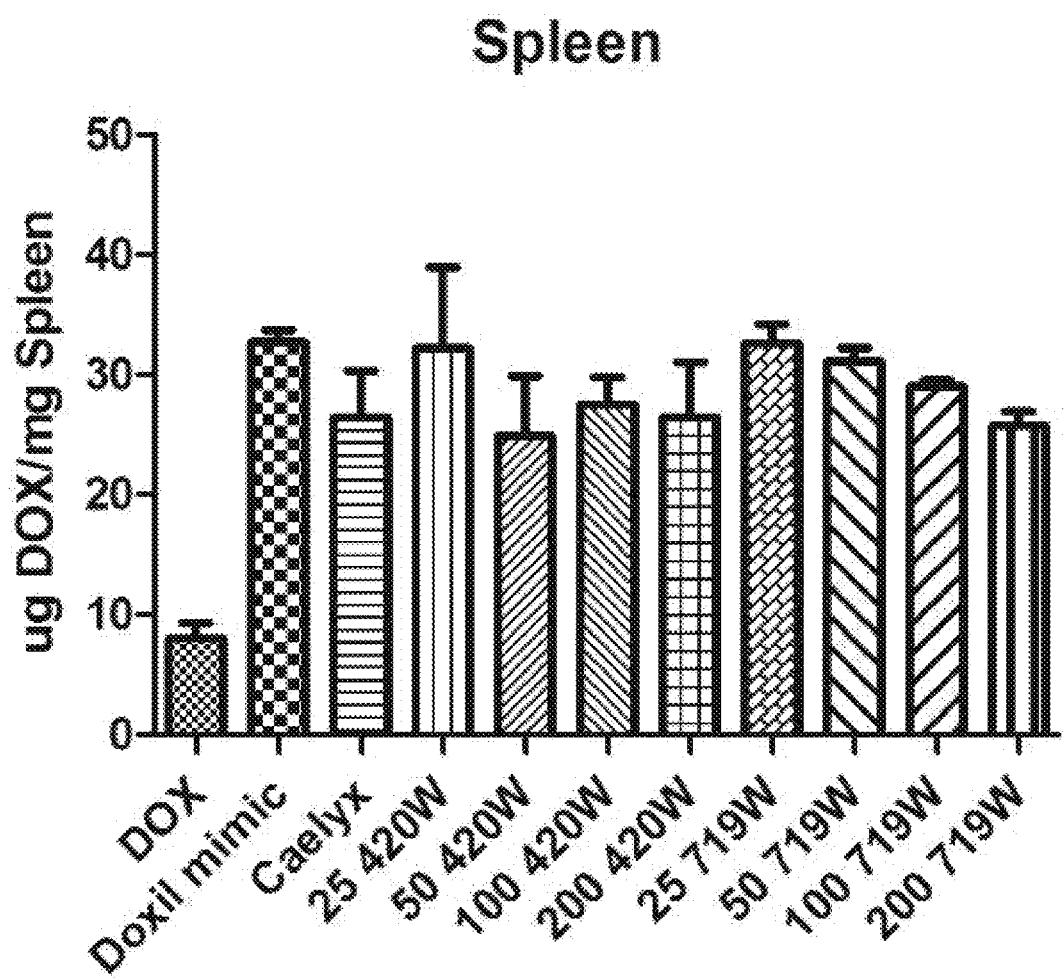
FIG. 7B illustrates the various liposomal composition bio-distribution results in BALB/c mice bearing TUBO tumor treated with a dose intravenous injection of 15 mg/kg liposomal DOX, in the spleen.
Figure 7C:
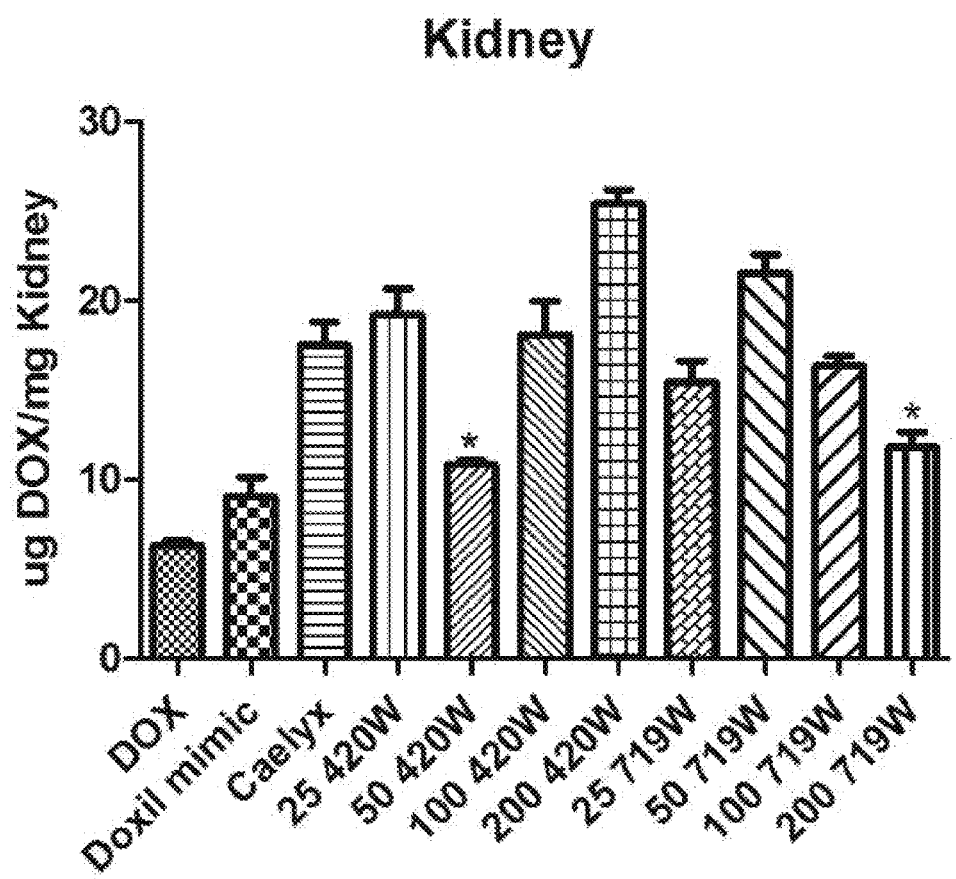
FIG. 7C illustrates the various liposomal composition bio-distribution results in BALB/c mice bearing TUBO tumor treated with a dose intravenous injection of 15 mg/kg liposomal DOX, in the kidney.
Figure 7D:
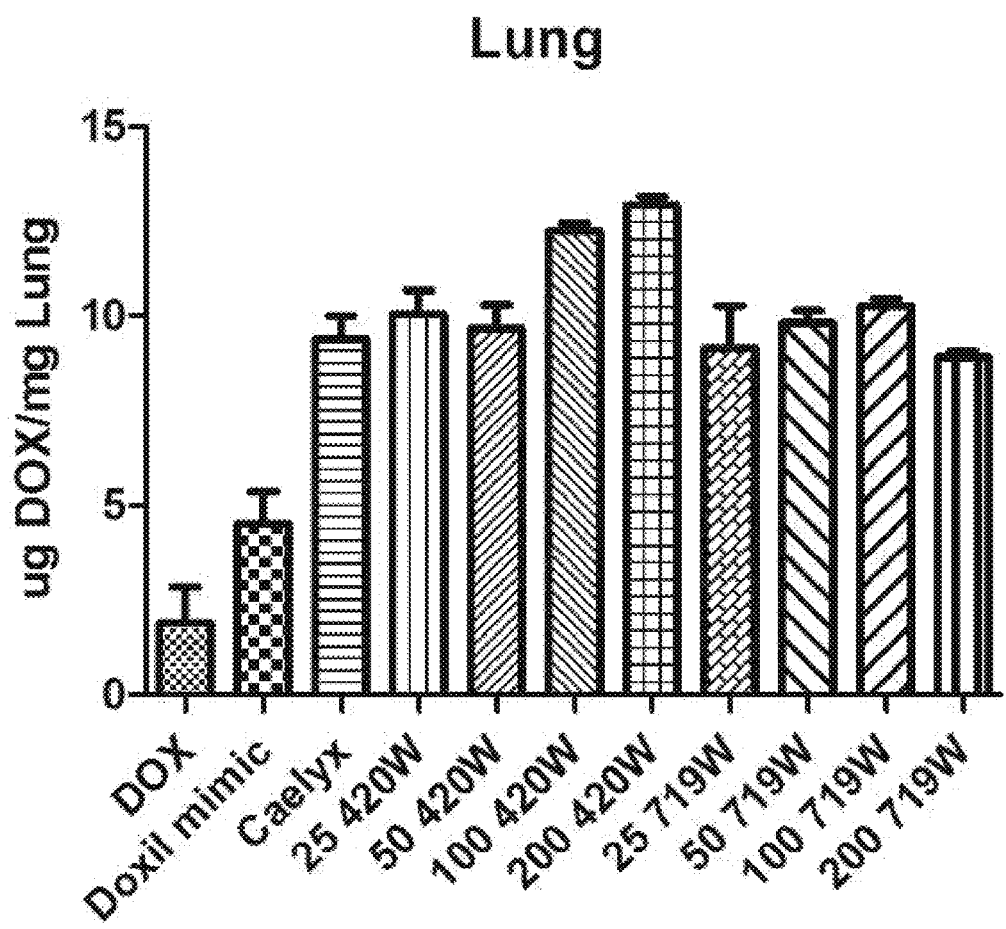
FIG. 7D illustrates the various liposomal composition bio-distribution results in BALB/c mice bearing TUBO tumor treated with a dose intravenous injection of 15 mg/kg liposomal DOX, in the lung tissues.
Figure 7E:
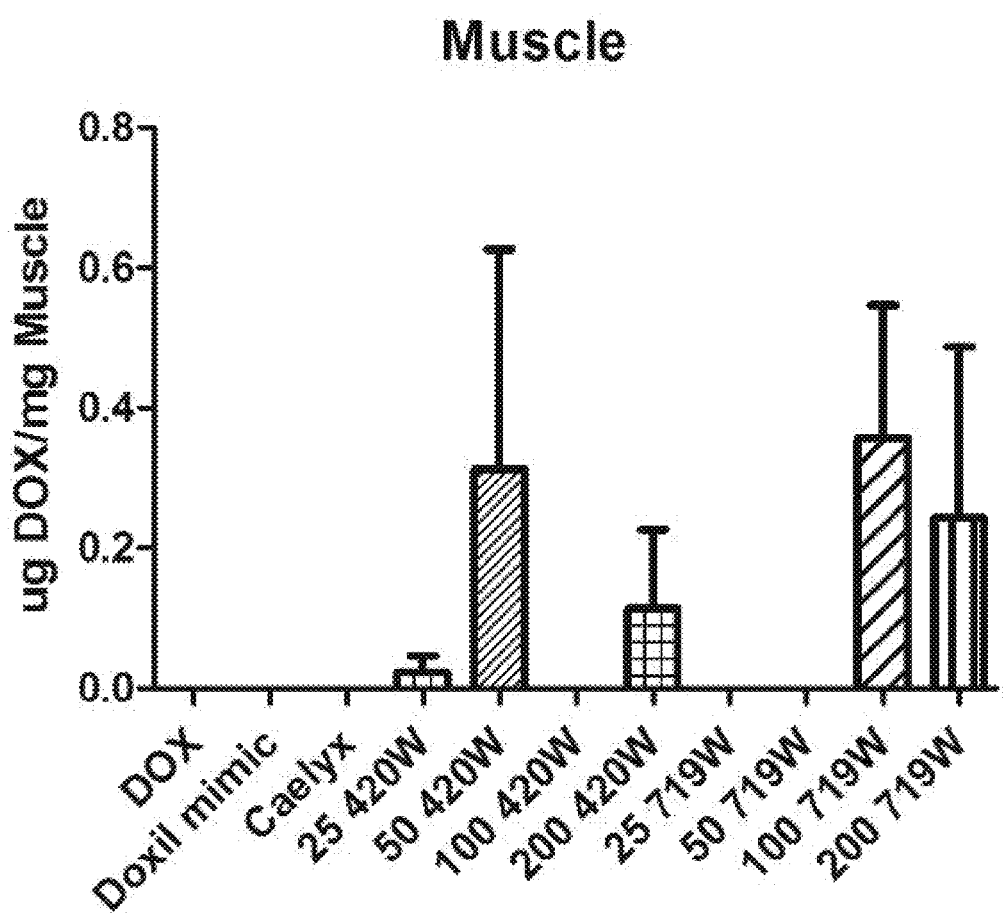
FIG. 7E illustrates the various liposomal composition bio-distribution results in BALB/c mice bearing TUBO tumor treated with a dose intravenous injection of 15 mg/kg liposomal DOX, in the muscle tissues.
Figure 7F:
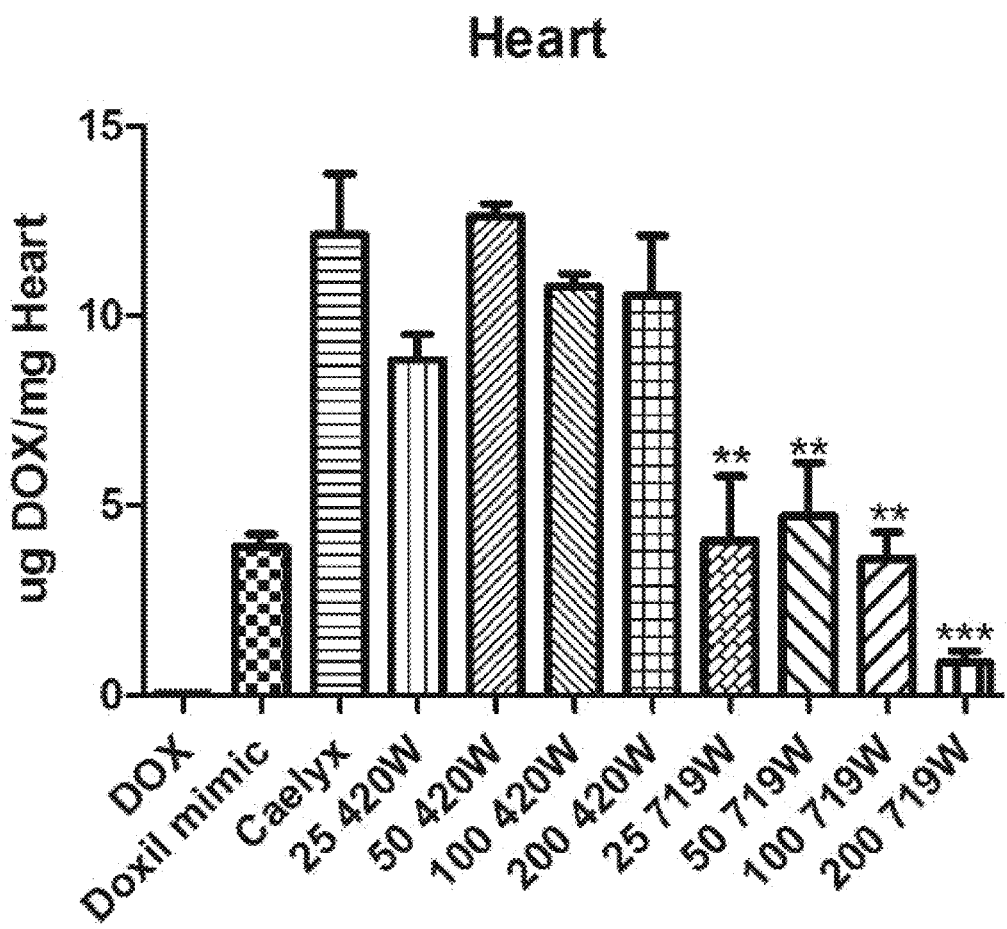
FIG. 7F illustrates the various liposomal composition bio-distribution results in BALB/c mice bearing TUBO tumor treated with a dose intravenous injection of 15 mg/kg liposomal DOX, in the heart tissues.

Referring now to FIG. 7A to FIG. 7F, these figures illustrate the various liposomal composition bio-distribution results in BALB/c mice bearing TUBO tumor treated with a dose intravenous injection of 15 mg/kg liposomal DOX, in the tissues including Liver (the results are illustrated in FIG. 7A); Spleen; (the results are illustrated in FIG. 7B); Kidney (the results are illustrated in FIG. 7C); and Lung tissues (the results are illustrated in FIG. 7D). The bio-distribution (DOX distribution) of liposomal composition in the above-mentioned tissues are used to analyze the reticuloendothelial system estimation (RSE). The results of liposomal composition bio-distribution in BALB/c mice bearing TUBO tumor treated with a dose intravenous injection of 15 mg/kg liposomal DOX in the non-tumoral tissues including muscle and heart are illustrated in FIG. 7E (muscle) and FIG. 7F (for heart). As illustrated in FIG. 7A to FIG. 7D, there is no significant difference in bio distribution between targeted and non-targeted liposomal compositions prepared in the present disclosure. These figures illustrate the DOX concentration as a part of peptide-liposome composition insignificantly distributed in spleen, lung and liver compared to Caelyx as a non-modified liposome. The LTVSPWY (SEQ ID NO: 1)-liposomes bearing 50 ligands, as well as MYWGDSHWLQYWYE (SEQ ID NO: 2)-liposomes bearing 200 ligands showed decreased DOX concentration in comparison with Caelyx. These results confirm once again low clearance and high concentrations of plasma in the peptide-liposome compositions compared to the non-targeted liposomes as well as free drugs, which occurs due to the small size of peptides and their invisibility to immune system. In general, higher blood concentration profile is excessively important in the targeting systems. This means the particles (herein peptide-liposomes) are hidden by the immune systems, having more circulating time and more contact with the targeted tissues. Therefore, the drug exposure time in targeting tissue will be increased, which resulted to significant therapeutic efficacy The lower uptake of peptide-liposome compositions by RES systems compared to the free drugs confirms less tendency of the peptide-liposomes to localize in the non-tumoral tissues and more accumulation in the tumor tissues as illustrated in FIG. 7E and FIG. 7F.

In the non-tumoral tissues, as illustrated in FIG. 7E and FIG. 7F, the heart and muscle tissues are considered as non-tumoral tissues to compare the bio-distribution results of the abovementioned tissues. According to the art, the heart tissues are considered as major site of doxorubicin (DOX) toxicity. However, as illustrated in FIG. 7F, there is no significant difference compared to the non-targeted liposome compositions.

In the case of using MYWGDSHWLQYWYE (SEQ ID NO: 2) peptide (denoted as 719W in the figures) in the liposome composition, there is even significant reduction of targeted liposomes compared to the non-targeted liposomes. (for peptide-liposomes bearing 25, 50, and 100 ligands P<0.01, 200 ligands P<0.001). This finding is a key factor in using peptides in clinical studies. Muscle as a normal and non-tumoral tissue as illustrated in FIG. 7E showed no significant differences in both targeted and non-targeted liposomes as their concentration is very low and even near to zero.

Therefore, with further reference to FIG. 7A to FIG. 7F, the less affinity to RES-rich organs and higher affinity to tumor is observed. In fact, these data confirmed the significant therapeutic efficacy or anti-tumor efficacy of these peptide-liposomes. Because a main aim of targeting is the best therapeutic efficacy that was achieved by long circulation time of drug and finally more exposure time to target tissue or tumor.

What is claimed is:

1. A liposomal composition, comprising:
   a molecule; and
   a lipid phase comprising a phospholipid, a PEGylated phospholipid, and cholesterol with molar ratio of between 50:30:5 and 60:40:5,
   wherein the molecule consists of a lipid conjugated to a peptide through at least one linker with a molar ratio of the peptide to the lipid of 1.2:1,
   wherein the peptide includes an amino acid sequence selected from the group consisting of LTVSPWY (SEQ ID NO: 1), MYWGDSHWLQYWYE (SEQ ID NO: 2), FCDGFYACYADV (SEQ ID NO: 3), IHNRYN-RFFYWY (SEQ ID NO: 4), PRWGDSHWLQYWYE (SEQ ID NO: 5), LMWGGSHWLEYWYE (SEQ ID NO: 6), GHWGDQHWLQYWYE (SEQ ID NO: 7), GWWGDSHWLQYWYE (SEQ ID NO: 8), LTVE-PWL (SEQ ID NO: 9), LTVSPLWD (SEQ ID NO: 11), LTVTPWL (SEQ ID NO: 12), LTVQPWP (SEQ ID NO: 13), LTVSPWT (SEQ ID NO: 14), VLTVQPW (SEQ ID NO: 15), LTVSLWT (SEQ ID NO: 16), PGVIPWN (SEQ ID NO: 17), LTYQTWP (SEQ ID NO: 18), and ELYVSRL (SEQ ID NO: 19), and
   wherein the molecule comprises a spacer at N-terminal or C-terminal of the peptide, said spacer is the amino acid sequence CGGG as set forth in SEQ ID NO: 10,
   wherein the liposomal composition comprises a plurality of liposomes, the plurality of liposomes comprising the molecule with a density between 25 and 200 molecules per liposome.

2. The liposomal composition of claim 1, wherein the peptide consists of the amino acid sequence consisting of LTVSPWY (SEQ ID NO: 1).

3. The liposomal composition of claim 1, wherein the peptide consists of the amino acid sequence consisting of MYWGDSHWLQYWYE (SEQ ID NO: 2).

4. The liposomal composition of claim 1, wherein the at least one linker comprises polyethylene glycol (PEG).

5. The liposomal composition of claim 1, wherein the lipid is selected from the group consisting of 1,2-Distearoyl-sn-Glycero-3-Phosphoethanolamine (DSPE), 2-Dioleoyl-sn-Glycero-3-Phosphoethanolamine (DOPE), and 1,2-di-palmitoyl-sn-glycero-3-phosphoethanolamine (DPPE).

6. The liposomal composition of claim 1, wherein the lipid comprises 1,2-Di stearoyl-sn-Glycero-3-Phosphoethanolamine-N-[Methoxy (Polyethylene glycol)-2000] (DSPE-PEG2000).

7. The liposomal composition of claim 1, wherein the phospholipid is selected from the group consisting of phosphatidyl cholines, phosphatidyl glycerols, and phosphatidyl ethanolamines.

8. The liposomal composition of claim 1, wherein the liposomal composition has an average diameter of about 100 nanometers or less.

9. The liposomal composition of claim 1, further comprising an active agent selected from the group consisting of cytotoxic/antitumor antibiotics, antimetabolites, anticancer agents, enzymes, detection agent, and combination thereof.

10. The liposomal composition of claim 9, wherein the cytotoxic/antitumor antibiotics is selected from the group consisting of daunorubicin, doxorubicin (DOX), epirubicin, idarubicin, mitoxantrone, valrubicin, carinomycin, nacetyladriamycin, rubidazone.

11. The liposomal composition of claim 9, wherein the active agent is doxorubicin (DOX).

12. A method for preparation of a peptide-liposome composition, the method comprising:

reacting a peptide with a lipid to synthesize a molecule;
preparing a liposome, the liposome comprising a phospholipid, a PEGylated phospholipid, and cholesterol with molar ratio of between 50:30:5 and 60:40:5;
loading an active agent onto the liposome; and
combining the molecule and the liposome to form the peptide-liposome composition with a density between 25 and 200 molecules per each liposome,
wherein the molecule comprises:
  a lipid;
  a peptide; and
  at least one linker between the lipid and the peptide,
wherein, the lipid is conjugated via the linker to the peptide with a molar ratio of peptide to lipid of 1.2:1,
wherein the peptide consists of an amino acid sequence selected from the group consisting of LTVSPWY (SEQ ID NO: 1), MYWGDSHWLQYWYE (SEQ ID NO: 2), FCDGFYACYADV (SEQ ID NO: 3), IHNRYNRFFYWY (SEQ ID NO: 4), PRWGDSHWLQYWYE (SEQ ID NO: 5), LMWGGSHWLEYWYE (SEQ ID NO: 6), GHWGDQHWLQYWYE (SEQ ID NO: 7), GWWGDSHWLQYWYE (SEQ ID NO: 8), LTVEPWL (SEQ ID NO: 9), LTVSPLWD (SEQ ID NO: 11), LTVTPWL (SEQ ID NO: 12), LTVQPWP (SEQ ID NO: 13), LTVSPWT (SEQ ID NO: 14), VLTVQPW (SEQ ID NO: 15), LTVSLWT (SEQ ID NO: 16), PGVIPWN (SEQ ID NO: 17), LTYQTWP (SEQ ID NO: 18), and ELYVSR (SEQ ID NO: 19), and
wherein the molecule comprises a spacer at N-terminal or C-terminal of the peptide, said spacer is the amino acid sequence CGGG as set forth in SEQ ID NO: 10.

13. The method of claim 12, wherein combining the molecule and the liposome is done by post attachment of the peptide to the liposome or post inserting of the peptide into the liposome.

14. The method of claim 12, wherein the active agent is selected from the group consisting of cytotoxic/antitumor antibiotics, antimetabolites, anticancer agents, enzymes and combinations thereof.

15. The method of claim 14, wherein the active agent is doxorubicin (DOX).

* * * * *